United States Patent
Levine

(10) Patent No.: US 7,794,726 B2
(45) Date of Patent: Sep. 14, 2010

(54) MUTANTS OF LYSINE DECARBOXYLASE, VACCINES FOR PERIODONTITIS, AND METHODS OF USE

(75) Inventor: Martin Levine, Norman, OK (US)

(73) Assignee: The Boards of Regents of the University of Oklahoma, Norman, OK (US)

(*) Notice: Subject to any disclaimer, the term of this patent is extended or adjusted under 35 U.S.C. 154(b) by 0 days.

(21) Appl. No.: 12/329,327

(22) Filed: Dec. 5, 2008

(65) Prior Publication Data

US 2009/0155296 A1 Jun. 18, 2009

Related U.S. Application Data

(60) Provisional application No. 61/005,693, filed on Dec. 7, 2007.

(51) Int. Cl.
A61K 39/02 (2006.01)
C12N 1/20 (2006.01)
C07H 21/02 (2006.01)
C12P 21/02 (2006.01)
C07K 14/00 (2006.01)

(52) U.S. Cl. ................ 424/190.1; 424/184.1; 435/69.1; 435/69.5; 435/69.7; 435/195; 435/252.33; 435/320.1; 435/488; 536/23.2; 536/23.5; 536/23.7; 536/24.5; 530/350

(58) Field of Classification Search ........................ None
See application file for complete search history.

(56) References Cited

U.S. PATENT DOCUMENTS

| | | | |
|---|---|---|---|
| 5,827,698 A | 10/1998 | Kikuchi et al. | |
| 6,103,220 A | 8/2000 | Levine | |
| 6,187,296 B1 | 2/2001 | Levine | |
| 6,576,435 B1 | 6/2003 | Levine | |
| 6,974,700 B2 | 12/2005 | Levine | |
| 2006/0270043 A1 | 11/2006 | Blattner et al. | |
| 2008/0213305 A1 | 9/2008 | Levine et al. | |

OTHER PUBLICATIONS

PCT/US08/85718, Levine (ISR), Mar. 11, 2009.
Lee et al., "Identification of essential active-site residues in ornithine decarboxylase of *Nicotiana glutinosa* decarboxylating both L-ornithine and L-lysine", *Biochem. J.* (Dec. 15, 2001) vol. 360, No. 3, pp. 657-665.
Levine et al., "An *Eikenella corrodens* Toxin Detected by Plaque Toxin-Neutralizing Monoclonal Antibodies", *Infec. Immun.* (May 1996) vol. 64, No. 5, pp. 1672-1678.
Yamamoto et al., "The *Escherichia coli ldcC* gene encodes another lysine decarboxylase, probably a constitutive enzyme", *Genes Genet Syst*, (Jun. 1997) vol. 72, No. 3, pp. 167-172.
PCT/US2007/25145, Levine et al. (ISR), Sep. 12, 2008.
Bowie et al., "Deciphering the Message in Protein Sequences: Tolerance to Amino Acid Substitutions" *Science*, vol. 247 (1990) pp. 1306-1310.
Greenspan et al., "Defining epitopes: It's not as easy as it seems", *Nature Biotechnology*, vol. 17 (Oct. 1999) pp. 936-937.
Hardham et al., "Evaluation of a monovalent companion animal periodontal disease vaccine in an experimental mouse periodontitis model", *Vaccine*, vol. 23 (2005) pp. 3148-3156.
Hardham et al., "Pigmented-anaerobic bacteria associated with canine periodontitis", *Veterinary Microbiology*, vol. 106 (2005) pp. 119-128.
Hatakeyama et al., "Expression pattern of adhesion molecules injunctional epithelium differs from that in other *gingival epithelia*", *J. Periodont. Res.*, vol. 41 (2006) pp. 322-328.
Levine et al., "Identification of lysine decarboxylase as a mammalian cell growth inhibitor in *Eikenella corrodens*: possible role in periodontal disease" *Microbial Pathogenesis*, vol. 30 (2001) pp. 179-192.
Li et al., "Identification of early microbial colonizers in human dental biofilm", *Journal of Applied Microbiology*, vol. 97 (2004) pp. 1311-1318.
Lindhe et al., "Plaque induced periodontal disease in beagle dogs", *J. Periodotal Res.*, vol. 10 (1975) pp. 243-255.
Listgarten et al., "Pathogenesis of periodontitis", *J. Clin. Periodontal*, vol. 13 (1986) pp. 418-425.
Loe et al., "Absence and Presence of Fluid from Normal and Inflamed Gingivae", *Periodontics*, vol. 3, No. 4 (Jul./Aug. 1965) pp. 171-177.
Marsh et al., "Are dental diseases examples of ecological catastrophes?", *Microbiology* vol. 149 (2003) pp. 279-294.
McAnally et al., "Bacteria reactive to plaque-toxin-neutralizing monoclonal antibodies are related to the severity of gingivitis at the sampled site", *Oral Microbial. Immunol.*, (Apr. 1993); 8(2):69-74 (abstract only).
Paquette et al., "Inhibition of experimental gingivitis in beagle dogs with topical salivary histatins", *J. Clin. Periodontal*, vol. 24 (1997) pp. 216-222.
Ramberg et al., "Bacterial colonization during de novo plaque formation", *J. Clin. Periodontal*, vol. 30 (2008) pp. 990-995.
Salonen et al., "Proliferative potential of the attached cells of human junctional epithelium" *J. Periodont. Res.*, vol. 29 (1994) pp. 41-45.
Sandmeier et al., "Multiple evolutionary origin of pyridoxal-5'-phosphate-dependent amino acid decarboxylases", *Eur. J. Biochem.*, vol. 221 (1994) pp. 997-1002.
Socransky et al., Microbial complexes in subgingival plaque, *J. Clin. Periodontal*, vol. 25 (1998) pp. 134-144.
Socransky et al., "Periodontal microbial ecology" *Periodontaology 2000*, vol. 38 (2005) pp. 135-187.
Tombelli et al., Modulation of clinical expression of plaque-induced gingivitis, *J. Clin. Periodontal*, vol. 31 (2004) pp. 239-252.

*Primary Examiner*—Robert B. Mondesi
*Assistant Examiner*—Padma V Baskar
(74) *Attorney, Agent, or Firm*—Dunlap Codding, P.C.

(57) ABSTRACT

The present invention is directed to mutants of lysine decarboxylase, nucleic acids encoding the mutants, and vaccines comprising the mutants for inhibiting and reducing the development of periodontal diseases, including gingivitis and chronic periodontitis. The vaccine composition comprises a recombinant lysine decarboxylase mutant which is based on a native version of the enzyme from *E. corrodens* and induces production of antibodies that inhibit the activity of the lysine decarboxylase enzyme in the oral cavity. The recombinant lysine decarboxylase mutant, in one version, comprises a mutation at residue 365 or at other locations within the active site, and in a preferred embodiment is produced from *E. coli* in large amounts and to form inclusion bodies. The purified inclusion bodies can then be used in the vaccine composition to induce in vivo production of antibodies that inhibit the activity of native *E. corrodens* lysine decarboxylase.

11 Claims, 6 Drawing Sheets

Blotted with goat anti-EC serum
(1 to 25,000)

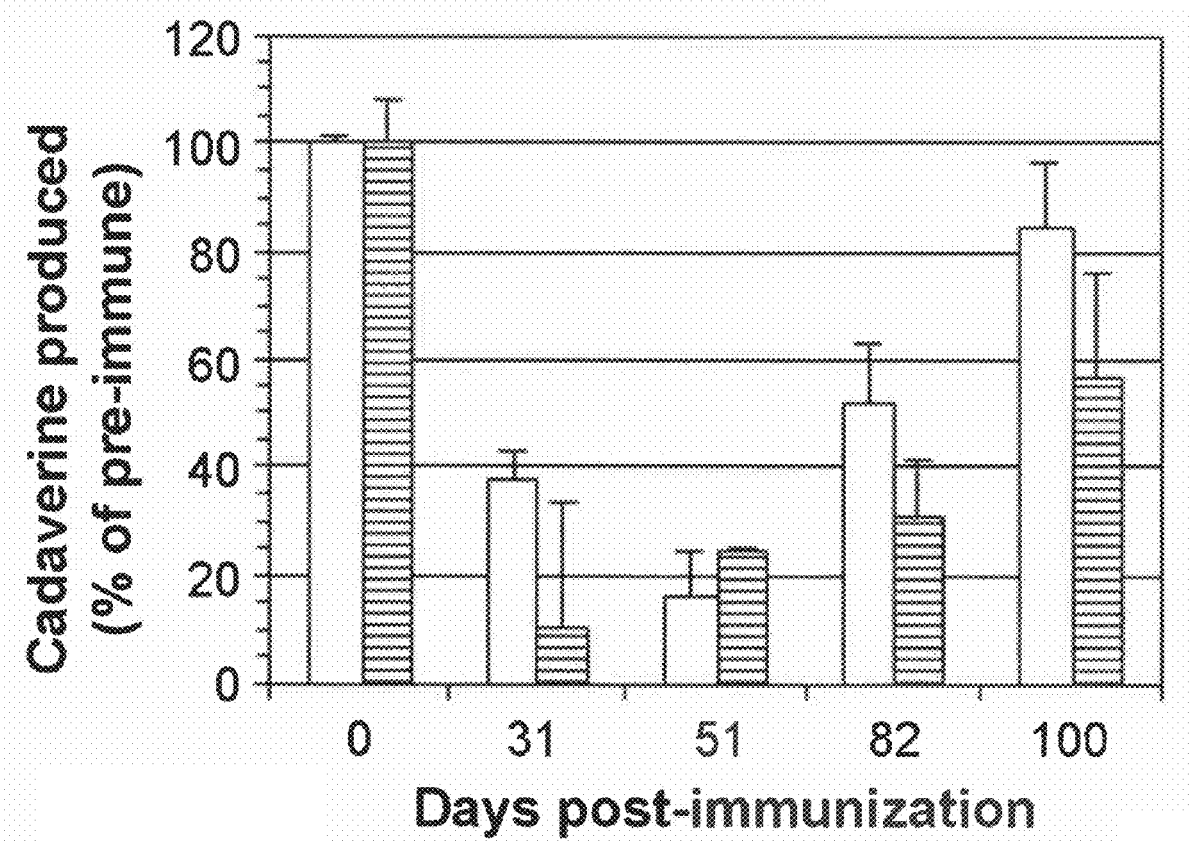

MUTANTS OF LYSINE DECARBOXYLASE, VACCINES FOR PERIODONTITIS, AND METHODS OF USE

CROSS-REFERENCE TO RELATED APPLICATIONS

The present application claims the benefit under 35 U.S.C. 119(e) of U.S. Provisional Application Ser. No. 61/005,693, filed Dec. 7, 2007, the entirety of which is hereby expressly incorporated herein by reference.

STATEMENT REGARDING FEDERALLY SPONSORED RESEARCH OR DEVELOPMENT

Some aspects of this invention were made in the course of Grant 1 R21 DE 14583-01 awarded by the National Institute of Dental Research Exploratory/Development Research and therefore the Government has rights in certain aspects of this invention.

BACKGROUND OF THE INVENTION

Periodontal disease refers to bacterially mediated inflammation of the gingiva (gingivitis) accompanied by a loss of periodontal attachment to one or more teeth (periodontitis). Gingivitis is detected by a red, swollen gingival margin that bleeds on gentle probing. Periodontitis is detected by exposure of the tooth's enamel-cemental junction and underlying cementum in the oral cavity, directly (recession) or within a deep gingival sulcus (pocket). Gingivitis and chronic periodontitis, by far the most common forms, are caused by bacteria that adhere to teeth and develop into a plaque (biofilm) that may become calcified at the gingival margin. In the late stages of periodontitis, so much support is lost that the teeth become loose and may exfoliate, creating a major problem for older humans and animals. The difficulty in chewing interferes with eating an adequate diet and the persistent bacterial colonization induces deleterious systemic effects throughout the body.

The gingiva is composed of free and attached portions. The free gingiva is the soft tissue side of the gingival sulcus, normally 1-2 mm in length. The sulcular side of the free gingiva is covered with oral sulcular epithelium and the oral cavity side with gingival epithelium. The free gingival margin is where these two epithelia meet in the oral cavity at the lip of the gingival sulcus. The gingival sulcus normally lies between tooth enamel above the cementum and oral sulcular epithelium and it extends from the free gingival margin to its base, the junctional epithelial attachment that covers gingival collagen fibers. The free gingiva is held tightly against the tooth by enclosed, free collagen fibers that extend from just below the enamel-cementum junction.

Periodontitis develops in association with persistent gingivitis caused by the plaque microbiota adhering to enamel. The bacteria extend apically along the enamel to the junctional epithelial attachment at its base. The junctional epithelium has an internal (inner) basal layer of dentally attached (DAT) cells that extend to the cemental-enamel junction. There it becomes continuous with an external (outer) epithelial basal layer that extends coronally in contact with the gingival stroma. Coronally it merges with the apical basal layer of oral sulcular epithelial cells. The dentally attached inner and stromally attached outer layers of the junctional epithelium enclose undifferentiated basal cells that, together with the two basal layers, comprise the dental-epithelial attachment.

The junctional epithelial keratinocytes have lax intercellular anchoring junctions and wide intercellular spaces [1]. Interstitial fluid therefore transudes from the underlying stroma through the entire epithelium to provide the DAT keratinocytes with nutrients necessary to support their proliferation and maintain their dental attachment[2]. The interstitial fluid transudes to the base of the sulcus where the most coronally situated DAT cells are susceptible to disruption of its nutrient content by lysine decarboxylase, a bacterial enzyme[3]. Lysine decarboxylase irreversibly converts lysine to cadaverine and carbon dioxide, depleting the lysine from the interstitial fluid in this region. The DAT cell proliferation at the junctional epithelial coronal extremity is inhibited. The affected DAT cells release mediators that convert the interstitial fluid into an inflammatory exudate containing neutrophilic granulocytes (neutrophils), the gingival crevicular fluid (GCF). Even healthy gingival sulci contain traces of GCF exudate. Exudation remains minimal because the flow stops whenever the coronal DAT cells are replenished with lysine.

Experimental human gingivitis is a well-established method of investigating the development of gingivitis[4]. During the first 6 hours after tooth cleaning, viridans streptococci along with *actinomyces* and other bacteria including *Eikenella corrodens* colonize the teeth of subjects who are free of gingivitis and periodontitis[5]. The commensal bacteria comprise a mostly gram positive microbiota that adheres to the gingival margin region of teeth in the oral cavity. The bacteria increase significantly and extend into the gingival sulcus over 4 additional days of no oral hygiene[6]. During this time, the GCF increasingly exudes from the gingival sulcus in association with microscopic evidence of inflammation[7].

The GCF contains serum proteins that are absent from interstitial fluid, and, because of its faster flow and inflammatory nature, it provides plasma proteins, glucose, amino acids and vitamins. Proteins are absent from the interstitial fluid, and their presence promotes the development of a gram negative microbiota within the initial plaque of commensal microbiota[8]. This gram negative microbiota, is termed the successor microbiota[9], and it is a major source of bacterial products that promote inflammation. Within the successor microbiota, *Porphyromonas gingivalis, Tanerella fosythensis* and *Treponema denticola* develop as a climax microbiota[9], but no one group or individual bacterium is exclusive to gingivitis or periodontitis; various bacteria may be involved.

Gram negative bacteria are a major source of lipopolysaccharide and many of the successor and climax microbiota perform asaccharolytic fermentations. During growth by asaccharolytic fermentation, energy is obtained by the bacteria hydrolyzing proteins to amino acids and metabolizing them anaerobically to ammonia and short chain fatty acids. The lipopolysaccharide and short chain fatty acids induce inflammation and the ammonia creates an alkaline environment, causing calcium phosphate in the GCF exudate to precipitate (calculus). The inflammation becomes evident as gingivitis which then induces the changes that cause periodontitis, especially if the bacteria remain sheltered from cleaning by calculus.

The GCF is an inflammatory exudate that provides the substrates for plaque mass to increase and for the successor microbiota to develop. If there was no GCF exudation, there would be no substrates for the successor microbiota to develop. Oral hygiene is essential to prevent the successor microbiota from developing on the GCF, but not the lysine decarboxylase induction of traces of GCF. Antibodies that inhibit all lysine decarboxylase activity in the oral cavity should therefore retard GCF exudation required for development of the successor and climax microbiota and therefore of gingivitis and chronic periodontitis.

The nutrients in GCF enable the colonies of commensal, gram positive bacteria to thicken at the gingival margin and lip of the sulcus, providing a more anaerobic environment for the successor microbiota to grow. But the GCF also replenishes lysine, causing the DAT cells to stop signaling until lysine again becomes depleted. These cycles of lysine depletion and GCF induction eventually permit enough of the successor microbiota to grow within the commensal bacteria at the gingival margin and extend into the sulcus. There, lipopolysaccharide and metabolic products of the successor microbiota induce gingivitis, which develops into periodontitis if it persists[10].

Untreated chronic periodontitis predominates in older humans, in whom it associates with a higher level of pro-inflammatory agents, including an increased risk of cardiovascular and cerebrovascular events and poor control of type II diabetes. Successful periodontal therapy reduces the level of pro-inflammatory agents and the associated risk of these diseases. In aging dogs and cats, bacterial products released from sites of periodontitis into the blood will spread throughout the body and may damage the kidneys, heart, liver and brain.

In humans, twice-daily oral hygiene slows the development of the successor microbiota, but cannot stop the lysine depletion cycles. In addition, professional cleaning every 3-6 months is necessary to remove bacterial plaque, especially if it has calcified. In cats and dogs, a hard diet controls plaque until calculus develops, usually by age 2, when annual scaling and prophylaxis is recommended. In the complete absence of oral hygiene, advanced periodontal disease develops and multiple tooth loss often results by late middle age.

Household pets such as dogs and cats develop severe periodontitis because advances in veterinary medicine have extended their life, and periodontitis has more time to advance. Unfortunately cleaning a household pet's teeth is expensive and undesirable because of a need for anesthesia. On the other hand, many bacterial diseases are efficiently and economically controlled by immunization. Immunization with an appropriate vaccine during a pet's early adolescence, before periodontitis has developed, and repeated immunization to maintain desirable antibody levels, may prevent periodontal disease and its associated illnesses. Immunization as a means of controlling periodontal disease therefore has commercial utility.

Advanced human periodontal disease is a common problem in many developing countries, where it often results in multiple tooth loss by early middle age. For humans, a vaccine as a prophylactic treatment or as an adjunct to therapy for gingivitis and periodontitis would reduce disease occurrence and recurrence and enhance quality of life. A vaccine given early in adolescence before the onset of periodontitis would also be useful for young adults who have poor access to dental care as well as those who follow poor dental hygiene. Therefore, a vaccine for preventing or modulating periodontal disease has economic and practical benefit.

A vaccine is commercially available that purports to control periodontitis in dogs. It consists of a mixture of cell wall and other components of bacterial species associated with periodontitis in dogs, a "Porphyromonas Denticanis-Gulae-Salivosa Bacterin", *P. gingivalis* is absent[11]. There are three shortcomings of this vaccine: (a) its control of dog periodontitis has not been demonstrated because it was tested in a mouse oral cavity where the vaccine inhibited periodontitis associated with artificial infection with only the component organisms[12]; (b) different gram negative bacteria may replace the inhibited bacteria in vaccinated dogs, causing periodontitis to persist; and (c) its many unknown components increase the likelihood of deleterious side effects. Evidence that this vaccine is safe and effective in dogs is uncertain.

SUMMARY OF THE INVENTION

The present invention is directed to mutants of lysine decarboxylase, nucleic acids encoding the mutants, and vaccines comprising the mutants for inhibiting and reducing the development of periodontal diseases, including gingivitis and chronic periodontitis. The vaccine composition comprises a recombinant lysine decarboxylase mutant which is based on a native version of the enzyme from *E. corrodens* and induces production of antibodies that inhibit the activity of the lysine decarboxylase enzyme in the oral cavity. The recombinant lysine decarboxylase mutant, in one version, comprises a mutation at residue 365 or at other locations within the active site, and in a preferred embodiment is produced from *E. coli* in large amounts and to form inclusion bodies. The purified inclusion bodies can then be used in the vaccine composition to induce in vivo production of antibodies that inhibit the activity of native *E. corrodens* lysine decarboxylase.

BRIEF DESCRIPTION OF THE DRAWINGS

FIG. 7 shows that the isolated mutant recombinant lysine decarboxylase inclusion body induces lysine decarboxylase inhibiting antibodies. Lysine decarboxylase activity was assayed directly in the presence and absence of 15% rabbit serum as reported for FIG. 4B. Inhibition to about 30% of pre-immune levels appeared within 10 days of the second immunization (day 31) and to about 25% 9 days after the third immunization (day 51). Inhibition was obvious at about 40% of pre-immune levels after another 30 days (day 82), but was clearly disappearing rapidly (day 100). Clear rectangles indicate rabbit 1 and filled rectangles indicate rabbit 2. Upper standard deviation levels are indicated above each rectangle.

DETAILED DESCRIPTION OF THE INVENTION

Figure 1:
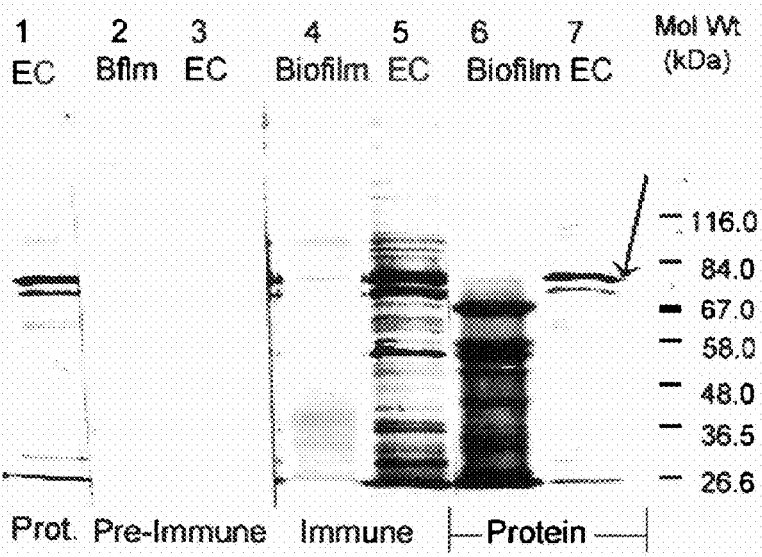
FIG. 1 shows detection of lysine decarboxylase protein by immune goat serum. Biorad Minigel and blotter used in 12% sodium dodecyl-polyacrylaminde gel electrophoresis (SDS-PAGE) followed by PVDF blotting, as suggested by the manufacturer. *E. corrodens* (1.7 µg), or biofilm extract (16.2 µg) were added to wells indicated. Blots were either stained for protein (Prot.) or blocked and reacted with pre-immune or immune goat serum used for the experiment in FIG. 2. Arrow indicates 80 kDa protein identified as lysine decarboxylase.

Before explaining at least one embodiment of the invention in detail by way of exemplary drawings, experimentation, results, and laboratory procedures, it is to be understood that the invention is not limited in its application to the details of the formulation, production, or uses of the compositions and methods as set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are hereby expressly incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the terms "nucleic acid", "nucleic acid segment", and "DNA segment" are used interchangeably and refer to a DNA molecule which has been isolated free of total genomic DNA of a particular species. Therefore, a "purified" DNA or nucleic acid segment as used herein, refers to a DNA segment which contains a coding sequence isolated away from, or purified free from, unrelated genomic DNA, genes and other coding segments. Included within the term "DNA segment", are DNA segments and smaller fragments of such segments, and also recombinant vectors, including, for example, plasmids, cosmids, phage, viruses, and the like. In this respect, the term "gene" is used for simplicity to refer to a functional protein-, polypeptide- or peptide-encoding unit. As will be understood by those in the art, this functional term includes genomic sequences, cDNA sequences or combinations thereof. "Isolated substantially away from other coding sequences" means that the gene of interest forms the significant part of the coding region of the DNA segment, and that the DNA segment does not contain other non-relevant large portions of naturally-occurring coding DNA, such as large chromosomal fragments or other functional genes or DNA coding regions. Of course, this refers to the DNA segment as originally isolated, and does not exclude genes or coding regions later added to, or intentionally left in, the segment by the hand of man.

Preferably, DNA sequences in accordance with the present invention will further include genetic control regions which allow the expression of the sequence in a selected recombinant host. The genetic control region may be native to the cell from which the gene was isolated, or may be native to the recombinant host cell, or may be an exogenous segment that is compatible with and recognized by the transcriptional machinery of the selected recombinant host cell. Of course, the nature of the control region employed will generally vary depending on the particular use (e.g., cloning host) envisioned.

Truncated genes also fall within the definition of preferred DNA sequences as set forth above. Those of ordinary skill in the art would appreciate that simple amino acid removal can be accomplished, and the truncated versions of the sequence simply have to be checked for the desired biological activity in order to determine if such a truncated sequence is still capable of functioning as required. In certain instances, it may be desired to truncate a gene encoding a protein to remove an undesired biological activity, as described herein.

Nucleic acid segments having a desired biological activity may be isolated by the methods described herein. The term "a sequence essentially as set forth in SEQ ID NO:X" means that the sequence substantially corresponds to a portion of SEQ ID NO:X and has relatively few amino acids or codons encoding amino acids which are not identical to, or a biologically functional equivalent of, the amino acids or codons encoding amino acids of SEQ ID NO:X. The term "biologically functional equivalent" is well understood in the art and is further defined in detail herein, as a gene or polypeptide having a sequence essentially as set forth in SEQ ID NO:X, and that is associated with the ability to perform a desired biological activity in vitro or in vivo.

The DNA segments of the present invention encompass DNA segments encoding biologically functional equivalent proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the protein or to test mutants in order to examine biological activity at the molecular level or to produce mutants having changed or novel enzymatic activity and/or substrate specificity. In particular, the nucleic acids and recombinant lysine decarboxylase of the present invention are intended to include mutants comprising codon or amino acid substitutions, particularly conservative substitutions such as are generally recognized in the art, at portions of the nucleic acid or protein which are not involved in the active site, substrate binding, or folding of the protein.

The term "polypeptide" as used herein is a generic term to refer to native protein, fragments, or analogs of a polypeptide sequence. Hence, native protein, fragments, and analogs are species of the polypeptide genus.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "recombinant" in the context of polypeptide coding regions and the polypeptides encoded by such coding regions refers to non-native products wherein the coding regions, and typically the expression thereof, have been manipulated in vitro by man to differ from their occurrence in nature. The polypeptides utilized in the methods of the present invention may be produced in a number of different recombinant systems known in the art, including but not limited to, archeal, prokaryotic, or eukaryotic systems. For expression in an appropriate expression system, the desired viral capsid polypeptide coding regions are operably linked into an expression vector and introduced into a host cell to enable expression. The coding region with the appropriate regulatory regions will be provided in proper orientation and reading frame to allow for expression. Methods for gene construction are known in the art. See, in particular, Molecular Cloning, A Laboratory Manual, Sambrook et al, eds., Cold Spring Harbor Laboratory, Second Edition, Cold Spring Harbor, N.Y. (1989) and the references cited therein.

As used herein, when the term "purified" is used in reference to a molecule, it means that the concentration of the molecule being purified has been increased relative to molecules associated with it in its natural environment. Naturally associated molecules include proteins, nucleic acids, lipids and sugars but generally do not include water, buffers, and reagents added to maintain the integrity or facilitate the purification of the molecule being purified. For example, even if mRNA is diluted with an aqueous solvent during oligo dT column chromatography, mRNA molecules are purified by this chromatography if naturally associated nucleic acids and other biological molecules do not bind to the column and are separated from the subject mRNA molecules.

As used herein, when the term "isolated" is used in reference to a molecule, the term means that the molecule has been removed from its native environment. For example, a polynucleotide or a polypeptide naturally present in a living animal is not "isolated," but the same polynucleotide or polypeptide separated from the coexisting materials of its natural state is "isolated", for example in the form of an inclusion body as contemplated herein. Further, recombinant DNA molecules contained in a vector are considered isolated for the purposes of the present invention. Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Thus, not all "isolated" molecules need be "purified."

The term "mutant" as used herein will be understood to include a gene or protein (polypeptide) that differs from a native sequence by one or more nucleotides or amino acids, respectively. When the term is utilized to describe a gene, the term "mutant" will refer to a gene that has one or more nucleotides that differ from a native gene sequence such that at least one amino acid of the protein or peptide encoded by the mutated gene differs from the native protein or peptide encoded by the native gene sequence. When the term is utilized to describe a protein or peptide, the term "mutant" will refer to a protein or peptide that has one or more amino acids that differ from the amino acid sequence of the native protein or peptide.

"Treatment" refers to both therapeutic treatment and prophylactic or preventative measures. Those in need of treatment include those already with the disorder as well as those in which the disorder is to be prevented.

When the terms "a" or "an" are used in this disclosure, they mean "at least one" or "one or more", unless otherwise indicated.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most host cell types at most times are commonly referred to as "constitutive promoters". New promoters of various types useful in plant cells are constantly being discovered; numerous examples may be found in the compilation by Okamuro and Goldberg, Biochemistry of Plants 15:1-82 (1989). It is further recognized that since in most cases the exact boundaries of regulatory sequences have not been completely defined, DNA fragments of some variation may have identical promoter activity.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or anti-sense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g.; Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

For purposes of the present invention, "complementarity is defined as the degree of relatedness between two DNA segments. It is determined by measuring the ability of the sense strand of one DNA segment to hybridize with the anti-sense strand of the other DNA segment, under appropriate conditions, to form a double helix. A "complement" is defined as a sequence which pairs to a given sequence based upon the canonic base-pairing rules. For example, a sequence A-G-T in one nucleotide strand is "complementary" to T-C-A in the other strand.

In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity between two amino acid sequences is defined as the presence of a series of exactly alike or invariant amino acid residues in both sequences.) The definitions of "complementarity", "identity" and "similarity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 .mu.g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37.degree. C. in a solution comprising: 20% formamide, 5.times.SSC (150 mM NaCl, 15 mM trisodium citrate), 50 mM sodium phosphate (pH 7.6), 5.times.Denhardt's solution, 10% dextran sulfate, and 20 mg/ml denatured sheared salmon sperm DNA, followed by washing the filters in 1.times.SSC at about 37-50.degree. C. The skilled artisan will recognize how to adjust the temperature, ionic strength, etc. as necessary to accommodate factors such as probe length and the like.

The present invention constitutes several embodiments. One embodiment is directed to a vaccine for inducing antibodies that inhibit lysine decarboxylase therefore providing a simple, inexpensive therapy to treat or prevent periodontal disease in mammals including humans, other primates, and dogs, in which periodontal disease most resembles that of humans. The major source of lysine decarboxylase in human and canine oral cavities appears to be *Eikenella corrodens*. In the present invention, the vaccine comprises one or more recombinant lysine decarboxylase mutants based on native lysine decarboxylase from *E. corrodens*.

More particularly, the present invention contemplates immunogenic compositions for inducing an immune response against lysine decarboxylase for treating or preventing periodontitis in a subject. Such compositions may comprise a vaccine and/or immunogen that comprises recombinant, mutated forms of lysine decarboxylase proteins, wherein such recombinant, mutated forms of lysine decarboxylase proteins are inactivated or substantially inactive so that such proteins do not exhibit significant lysine decarboxylase activity. In one embodiment, the mutated lysine decarboxylase protein comprises in a preferred embodiment, an amino acid residue (alanine) in place of the lysine at position 365 (K365→A365) of the native lysine decarboxylase protein (SEQ ID NO:2) encoded by E. corrodens. The mutated protein, comprises at least one substituted amino acid residue within the sequence of amino acid residues 360 to 370 of SEQ ID NO:2, i.e., which substantially comprises the active site of the protein.

The vaccine of the present invention comprises, in a preferred embodiment, a recombinant lysine decarboxylase mutant preferably as a component of a purified, isolated inclusion body. Except for the replacement of an alanine at position 365 of the catalytic site, this recombinant lysine decarboxylase mutant polypeptide is identical to the E. corrodens lysine decarboxylase and induces effective protection from gingivitis as described herein. The recombinant nucleic acid which encodes the recombinant lysine decarboxylase mutant preferably comprises modifications to improve its expression in an expression system such as E. coli.

More particularly, the lysine decarboxylase mutant of the present invention comprises a polypeptide having an amino acid substitution at least one of positions 360, 361, 362, 363, 364, 365, 366, 367, 368, 369 and 370 of SEQ ID NO:2, wherein the substituted residue at the above positions is one of gly, val, ala, leu, ile, phe, tyr, thr, ser, asp, asn, glu, gln, pro, his, lys, arg, met, trp, and cys (as long as it is different from the native residue), such that the enzymatic activity of the mutant is diminished by at least 50% relative to the activity of native lysine decarboxylase of E. corrodens in accordance with the assay for lysine decarboxylase activity described herein. The mutant lysine decarboxylase of the present invention is further contemplated to comprise a polypeptide having at least 95% identity with the lysine decarboxylase having SEQ ID NO:2, as long as it has a substitution in the active site therein (positions 360-370). Preferably the substitution is non-conservative.

The invention further comprises an isolated mutant lysine decarboxylase polypeptide, comprising an amino acid sequence having at least about 95% sequence identity, or at least about 96% sequence identity, or at least about 97% sequence identity, or at least about 98% sequence identity, or at least about 99% sequence identity to a polypeptide having SEQ ID NO:2 comprising a substitution in at least one of positions 360-370, thereof.

In one aspect, the isolated nucleic acid molecule of the present invention comprises a nucleotide sequence having at least about 95% sequence identity, or at least about 96% sequence identity, or at least about 97% sequence identity, or at least about 98% sequence identity, or at least about 99% sequence identity to a DNA molecule encoding a lysine decarboxylase mutant having a substitution at least one of positions 360-370 of SEQ ID NO:2, or a nucleic acid sequence complementary to the above-sequence.

The present invention further comprises nucleic acids which hybridize under conditions of high stringency or moderate stringency to the nucleic acids described herein which encode the lysine decarboxylase mutants of the present invention.

For example, the present invention includes an isolated nucleic acid sequence or fragment thereof which hybridizes, under moderate or high stringency conditions, to a nucleic acid sequence which encodes a mutant of SEQ ID NO:2 having a substitution in at least one of positions 360-370 thereof.

The present invention also encompasses an isolated nucleic acid or fragment thereof, which hybridizes, under moderate or high stringency conditions, to an isolated nucleic acid sequence encoding a polypeptide which has at least 95% identity to an amino acid sequence SEQ ID NO:2 having a substitution at position 365 thereof.

Where the invention contemplates a vaccine, the immunogenic composition preferably further includes a pharmaceutically acceptable adjuvant, carrier, and/or excipient in which the proteins described herein above are disposed and/or associated.

In general, the present invention also includes methods of producing the immunogenic compositions described herein. Such methods include inserting the mutant lysine decarboxylase nucleic acid into a host cell (preferably E. coli), thereby creating a recombinant host cell encoding the mutated lysine decarboxylase. The recombinant host cell is then grown under conditions that allow for expression of the mutated lysine decarboxylase, and the mutated lysine decarboxylase is then purified from the recombinant host cell.

The present invention further includes a method of inducing an immunogenic response in a subject, comprising administering at least one of the immunogenic vaccine compositions described herein to the subject.

The present invention in one embodiment is thus directed to a vaccine against lysine decarboxylases, particularly those from E. corrodens, the vaccine thus comprising an entire lysine decarboxylase mutant thereof, or an immunogenic portion thereof.

Although protein antigens usually induce a strong antibody response, immunity lasts much longer when given with an adjuvant, a viscous homogeneous material that provides a small region of highly concentrated antigen to stimulate the immune system. The adjuvant can be purchased as a sterile, pyrogen-free 3% aluminum hydroxide gel (Alhydrogel), for example, which is stable at room temperature, has a uniformly high adsorption capacity, especially in the absence of multivalent ions such as phosphate. Alhydrogel (Accurate Chemical & Scientific Corp., Westbury N.Y.) is stable for several years and adverse reactions to it have not been observed in dogs or humans.

The present invention further contemplates a method of producing a polypeptide comprising the steps of providing a vector comprising a nucleic acid comprising or complementary to a nucleotide sequence encoding a polypeptide comprising a variant of SEQ ID NO:2 having at least one substitution in one of positions 360-370 thereof, or a polypeptide having at least 95% identity to said variant, the nucleic acid of the vector operably linked to a promoter, the vector introduced into a host cell, and causing expression of the nucleic acid to produce the polypeptide within the host cell under suitable conditions sufficient for said expression.

The host cell may be, for example, a eukaryotic cell or a prokaryotic cell. In particular, the prokaryotic cell may be, for example, E. coli, cyanobacteria, Spirulina spp. or B. subtilis. The eukaryotic cell may be, for example, a mammalian cell, an insect cell, a plant cell or a fungal cell (e.g., a yeast cell such as Saccharomyces cerevisiae, Saccharomyces carlsbergensis, Candida spp., Lipomyces starkey, Yarrowia lipolytica, Kluyveromyces spp., Hansenula spp., Trichoderma spp. or Pichia spp.). Other fungal hosts such as Rizopus spp., Aspergillus spp. and Mucor spp. may also be utilized.

Moreover, the present invention also includes a vector comprising: an isolated nucleotide sequence comprising or complementary to a nucleotide sequence encoding a polypeptide as contemplated herein, operably linked to a regulatory sequence (e.g., a promoter). The invention also includes a host cell comprising this vector. The host cell may be, for example, a eukaryotic cell or a prokaryotic cell. Suitable eukaryotic cells and prokaryotic cells are as defined herein.

As noted herein, once the vector has been constructed, it may then be introduced into the host cell of choice by methods known to those of ordinary skill in the art including, for example, transfection, transformation and electroporation (see Molecular Cloning: A Laboratory Manual, 2.sup.nd ed., Vol. 1-3, ed. Sambrook et al., Cold Spring Harbor Laboratory Press (1989)). The host cell is then cultured under suitable conditions permitting expression of the genes leading to the production of the lysine decarboxylase mutant, which is then recovered and purified.

EXAMPLES

Examples are provided hereinbelow. However, the present invention is to be understood to not be limited in its application to the specific experimentation, results and laboratory procedures of the examples. Rather, the examples are simply provided as among several of many embodiments of the invention and are meant to be exemplary, not exhaustive.

Example I

Producing Lysine Decarboxylase Inhibiting Antibodies

In one experiment, a cell-surface extract of *E. corrodens* containing about 25% lysine decarboxylase protein was used to immunize two goats (0.25 mg of protein from this *E. corrodens* extract after emulsification in 50% (v/v) Freunds complete adjuvant). The injections at 10-12 multiple subcutaneous sites on the back were repeated after 2 and 4 weeks using Freunds incomplete adjuvant. Goats were bled before immunization and two weeks after the last injection. The blood was clotted overnight at 0° C. to obtain pre- and post-immune serum. Enzyme activity was assayed in the presence or absence of 50% (v/v) serum, and *E. corrodens* extract was obtained as described elsewhere herein.

Figure 2:
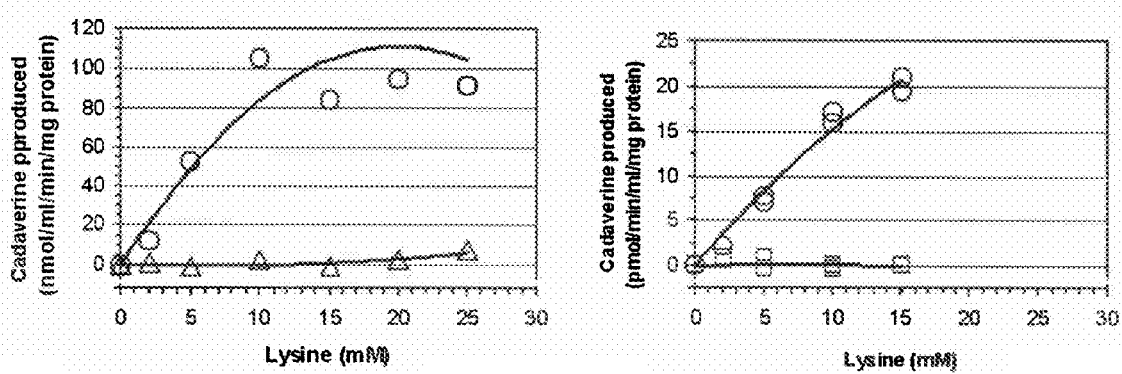
FIG. 2 shows the effect of immune or pre-immune goat serum on cadaverine production by *E. corrodens* or plaque extracts. Symbols: Unimmunized goat (or pre-immune serum) □-□; Immunized goat □-□ and □-□. Inhibition was retained for up to 9 months if immune serum was not frozen, but simply stored at 4° C. Goats were immunized with 0.25 mg *E. corrodens* extract in Freunds adjuvant.

Controls (no serum or pre-immune serum only) gave an asymptotically increasing amount of cadaverine as the lysine concentration increased from 0 to 25 mM. Maximal catalysis was 80-120 nmol cadaverine/min/mg protein/ml for *E. corrodens* extract and 0.03% of that for plaque pooled from the gingival region of teeth. Immune serum from both goats detected lysine decarboxylase on immunoblots (FIG. 1) and inhibited all activity in both *E. corrodens* and plaque extracts (FIG. 2), whereas pre-immune antibodies neither detected lysine decarboxylase nor inhibited its activity. The inhibiting power of goat antibodies was stable for at least 5 months.

Example II

Immunization of Dogs with Lysine Decarboxylase from *E. Corrodens* Protects from Gingivitis A soft diet causes gingivitis to develop within 6 weeks in 1-2 year old beagle dogs that are free of gingivitis and periodontitis[13, 14]. This model of gingivitis development was used in a pilot study to determine whether immunization with lysine decarboxylase purified from *E. corrodens* indeed inhibits plaque and gingivitis development in small 1-year old beagle dogs.

*E. corrodens* type strain (ATCC 23834) was grown for 64 h in 3 liters of autoclave-sterilized trypticase soy broth (VWR-Scientific Products, Irving Tex.), supplemented with Millipore filter sterilized sodium bicarbonate (5 mg/mL), potassium nitrate (2 mg/mL) and hemin (0.5 mg/mL). After 65 h growth at 37° C., the cell pellet was obtained by centrifugation, washed twice with physiological phosphate buffered saline and weighed. About 2.0 g wet weight was obtained and 4-times that wet weight of 65 mM NaCl was added. The enzyme was rubbed off the bacterial cell surface using 20 up-and-down strokes of a rapidly rotating Potter-Elvehjem pestle in a tight-fitting vessel [3]. The homogenate was centrifuged and the *E. corrodens* extract (supernatant) was sterilized by passage through a 0.2 µ Millipore filter membrane. The protein content of the extract was 0.5 mg/ml.

Small Beagle dogs aged 1.2 years were maintained on a hard Purina chow diet and received the vaccine subcutaneously into the skin on the back of the neck. Dogs 2 and 3 received 1.0 ml of extract containing 0.2 mg protein in 65 mM NaCl and suspended in 0.3% Rehydragel HPA (Reheis, Inc., 235 Snyder Ave, Berkeley Heights, N.J. 07922). Dogs 1 and 4 received the same preparation without *E. corrodens* extract (controls). Immunizations were repeated after three and six weeks.

On the day of the first injection, the teeth of all four dogs were scaled and polished and toothbrushing was begun daily. During the second week after immunization, toothbrushing was stopped and the dogs were switched for 5 days to a soft (canned) Purina chow for plaque to accumulate The plaque was collected and its lysine decarboxylase activity was determined as the cadaverine molar fraction of lysine plus cadaverine content (details described in U.S. Patent Publication 2008/0221803 A1). The teeth were again scaled and polished and the hard chow diet and daily toothbrushing were re-instituted for another 9 weeks and 1 day (total of 77 days after the first immunization).

The cadaverine fraction of the collected plaque was small, 2.5% (standard deviation 1.1%). The plaque was already calcified at the sulcus and it is not clear whether the soft (uncalcified) sampled values were representative of plaque at the gingival sulcus. In 4 other dogs with periodontitis (ages 8-11), the mean cadaverine fraction was about 3 times greater.

Figure 3:
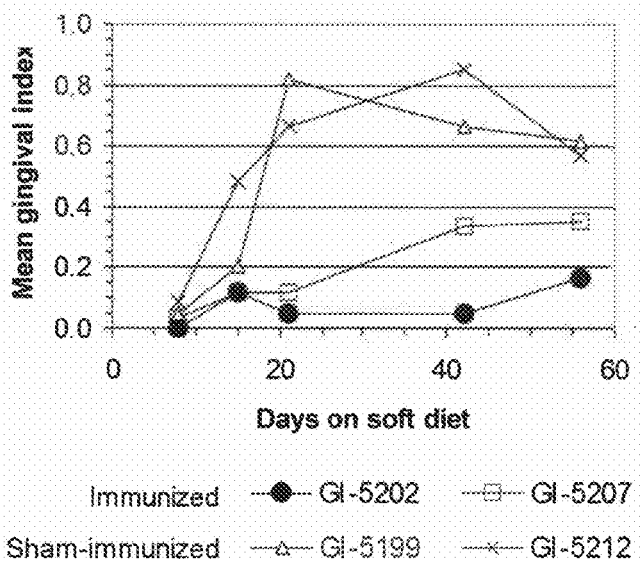
FIG. 3 shows the effect of immunization with lysine decarboxylase from *E. corrodens* ATCC 32834 on gingivitis and plaque development. The change to a soft diet began 77 days after the first immunization (day 0, see text). All plaque was removed at that time and so the plaque score was zero. Symbols: immunized (dog 2), ●-●; immunized (dog 3), □-□; sham immunized (dog 1), Δ-Δ; sham immunized (dog 4), x-x. A: Effect on GI. B: Effect on P/I. C: Relationship between GI and PlI. Regression equation is GI=1.15*P/I−0.47; $R^2$=0.57, p<0.001.
Figure 3:
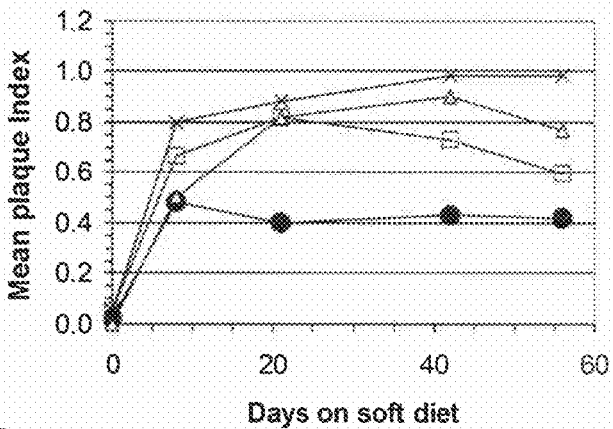
Figure 3:
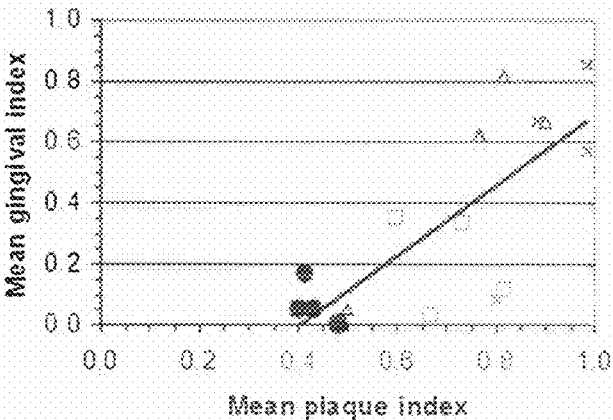

At day zero (77 days after the initial immunization and 35 days after the last immunization), plaque and gingivitis scores (PlI and GI) were measured on the mesio-buccal, buccal and disto-buccal surfaces of the canines and 4 premolars on all 4 quadrants (60 sites/dog) and the teeth again scaled and polished. Toothbrushing was stopped and the dogs were moved permanently to the soft diet to induce plaque and gingivitis. PlI and GI measurements were then recorded weekly for 4 weeks and then at weeks 6 and 8. At day 0, the plaque index (PlI) was similar in all 4 dogs (0.00 to 0.05) because of the daily brushing, but the mean GI of the two immunized dogs was 0.03, whereas that of the sham-immunized dogs was 0.12 and 0.45. Thus, even on the hard diet, before testing for gingivitis development in the beagle model, the immunized dogs had less gingivitis. Mean gingival and plaque index (GI) scores were graphed against days on the soft diet. The immunized dogs had little or no gingivitis through day 20 and then the gingivitis increased somewhat, but not as much as in the sham-immunized dogs (FIG. 3A). PlI also increased less in immunized than sham-immunized dogs (FIG. 3B) and correlated with GI (FIG. 3C).

Figure 4:
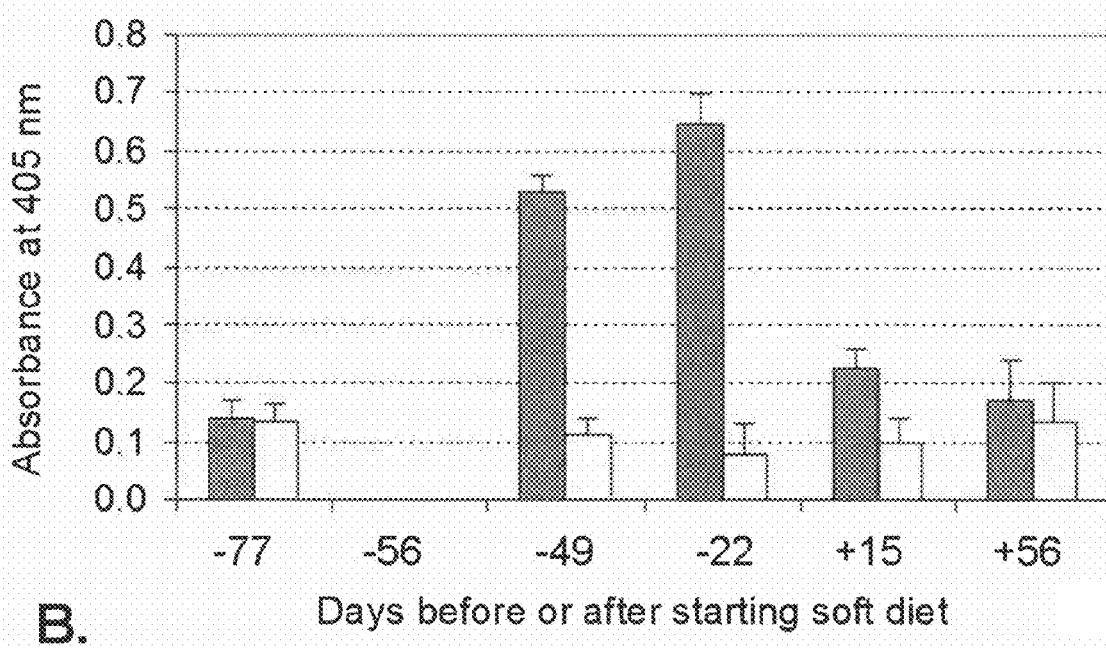
FIG. 4 shows the antibody response of dogs immunized with lysine decarboxylase from *E. corrodens* ATCC 32834. A: ELISA. Plates were coated with 0.25 mg/mL antigen and reacted with antiserum from all 4 dogs at the days indicated. Day −77 was the $2^{nd}$ October, date of the first immunization (see text). Means and upper standard deviations are shown. Immunized dogs—Dark columns; Sham immunized—Light columns. B: Antibody-mediated inhibition of lysine decarboxylase. Lysine decarboxylase activity was assayed directly in the presence and absence of 15% dog serum without trichloroacetic acid precipitation[3]. Inhibition was complete 49 and 22 days before day zero and was decreased thereafter. Control dog serum did not inhibit enzyme, like the pre-immune serum from all four dogs (day −77). After adding potassium carbonate and trinitrobenzene sulfonic acid (see text), the mixture was centrifuged for 10 min at 10,000 rpm prior to toluene extraction and assay.
Figure 4:
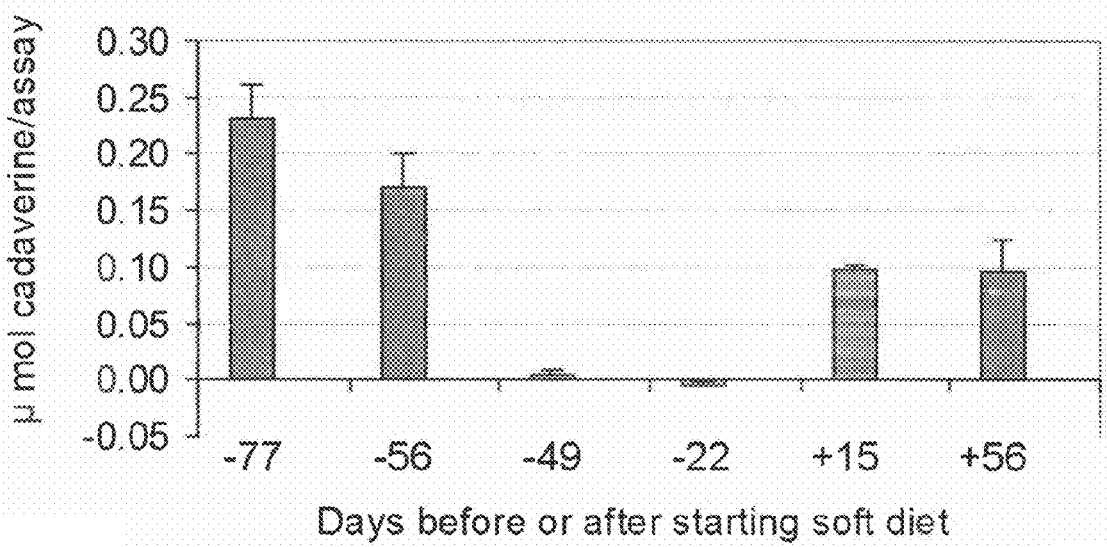

A marked IgG antibody response to antigen was detected 7 and 34 days after the first and second booster injections were completed (days −49 and −22; ELISA assays in FIG. 4A). The immune dog serum completely inhibited enzyme activity at these times (FIG. 4B). FIG. 4 also shows that, after 15 days or more on the soft diet, the IgG response decreased at least 3 fold and inhibited the enzyme activity less completely. The decrease in protection from gingivitis after day 20 on the soft diet followed the decrease in antibody content and its inhibition of enzyme activity.

These results show that immunization with wild-type lysine decarboxylase from *E. corrodens* is short-lived, but protects the dogs from gingivitis.

Example III

Recombinant DNA Encoding Lysine Decarboxylase

Because amounts of lysine decarboxylase, protein obtained from *E. corrodens* are too small for commercial use, the present invention also contemplates a method for obtaining a recombinant lysine decarboxylase protein and/or a mutant thereof that is strongly expressed by *E. coli*. Recombinant lysine decarboxylase protein to be used as an immunogen in the vaccine was produced, using the pET plasmid system, developed at Brookhaven National Laboratory under contract with the U.S. Department of Energy. The system expresses recombinant lysine decarboxylase in *E. coli* if induced by adding IPTG or lactose to the bacterial culture. This system is sold under the Novagen label, a subsidiary of EMD Biosciences Inc., San Diego, Calif. Other plasmid and host systems for producing recombinant lysine decarboxylase protein may also be used.

The *E. corrodens* lysine decarboxylase gene (SEQ ID NO:1) encodes native lysine decarboxylase protein (SEQ ID NO:2). SEQ ID NO:1 is derived from *E. corrodens* ATCC 32834.

In a preferred embodiment of the present invention, the coding sequence of the native lysine decarboxylase gene (SEQ ID NO:1) was changed to comprise preferred *E. coli* codons for optimized expression therein. This optimized nucleotide sequence gene (SEQ ID NO:3) was artificially synthesized with added NdeI and BamH1 restriction site extensions at each end and ligated into pET11a, which carries a gene for ampicillin resistance. The recombinant pET11a was transformed into the expression host, *E. coli* strain BL21 (DE3). Only the *E. coli* cells containing the plasmid with the lysine decarboxylase gene grows on medium containing ampicillin. These procedures are commercially available from Genscript Corp., 120 Centennial Ave. Piscataway, N.J.

Expression and Detection of Recombinant Lysine Decarboxylase.

A pET11a transformed *E. coli* BL21(DE3) was selected from an individual colony that grows on a Petri dish containing LB agar and 0.05 mg/ml ampicillin. Representative colonies were picked, inoculated into 3 ml of liquid LB containing 0.3 mg ampicillin (0.1 mg/ml) and cultured at 37° C. for 16 hours with shaking at 200 rpm. This culture was added to inoculate 25-100 ml of fresh LB medium containing 2.5 mg of ampicillin. Alternatively the 3 ml culture may be inoculated into a liter or more of LB/ampicillin medium if commercial amounts of recombinant antigen are required. Growth at 37° C. with aeration, for example shaking a 25 ml flask at 200 rpm, was performed until an optical density of 0.7±0.1 at 600 nm was attained (about 3 h). Recombinant antigen expression was then induced by adding 12.5 µmol of IPTG for 3 h. Un-induced (control) cultures had no IPTG added.

Figure 5:
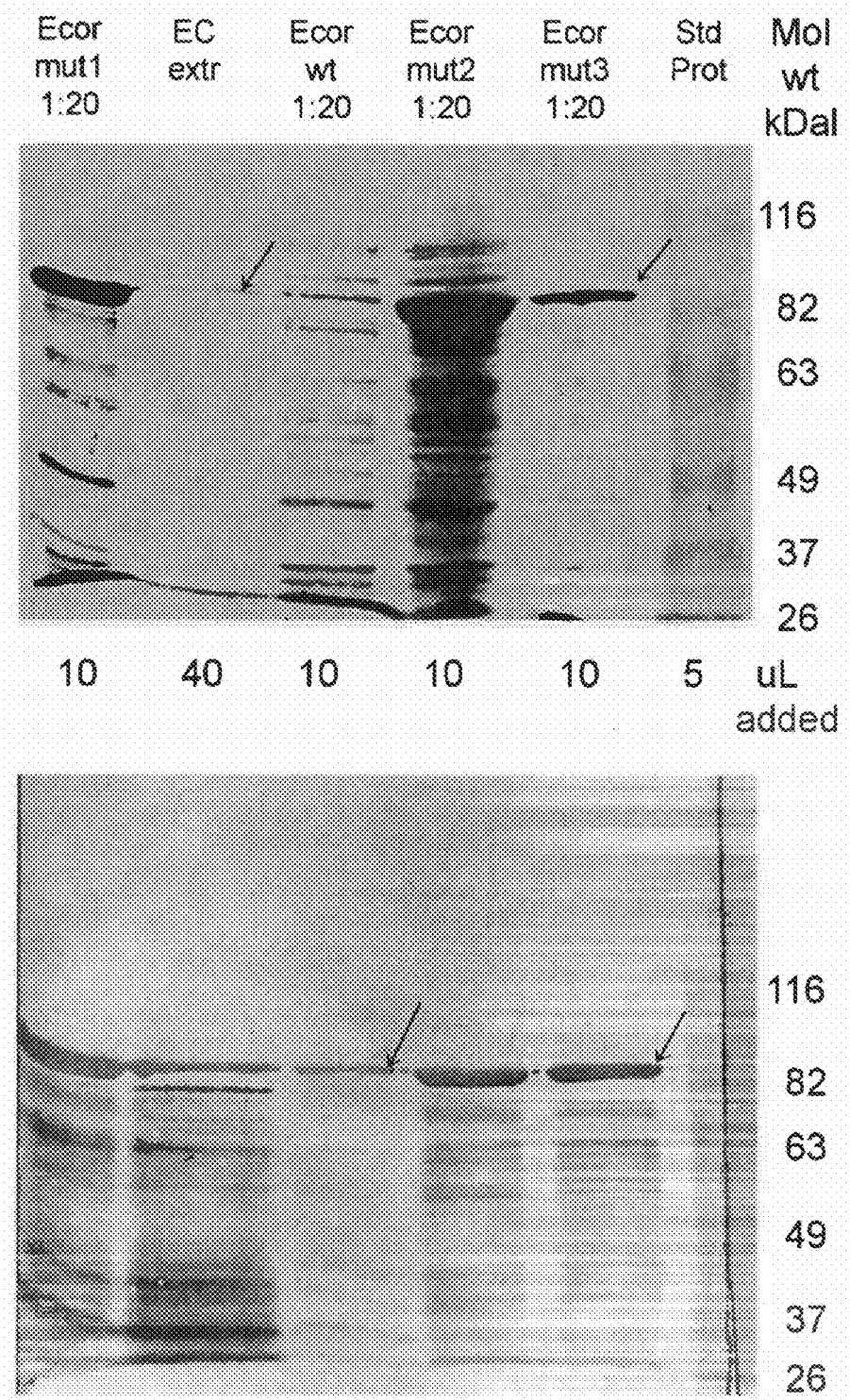
FIG. 5 shows blots of wild type (Ecor wt) and mutant (Ecor mut) lysine decarboxylase expressed in *E. coli*. Top: Protein stained blot. Bottom: Western immunoblotted with goat immune goat serum. Ecor wt and Ecor mut preparations were diluted 1 to 20 and 10 µL was added. The EC extract similar to that shown in FIG. 1, columns 1, 5 and 7 was not diluted and 40 µL (5 µg protein) was added to the gel. Arrows indicate the position of lysine decarboxylase.

After induction, 1 ml aliquots were removed from the large culture into microfuge tubes and centrifuged at 12,000 rpm for 2 min at 4°. The liquid supernatant was removed and 50 µL of cold (4° C.) 25 mM Tris-Cl, pH 8.0 was added to re-suspend each pellet. Following centrifugation and supernatant removal as before, the pellets were frozen for at least 30 min at −80°. The presence of lysine decarboxylase in the pellet was detected by sodium dodecyl polyacrylamide gel electrophoresis (SDS-PAGE). The *E. coli* pellet was removed from the freezer, thawed (1 or 2 minutes) and re-suspended in 40 µL lysis buffer (0.05 M Tris, pH 8.0, 5 mM $MgCl_2$, 50 µg/mL RNase A, 10 µg/mL DNase I). Lysozyme (1 µL of 50 mg/mL) was added to the suspension, which dissolved on incubation at room temperature for 15 minutes. An equal volume of sample buffer (1.0 mL 0.5M Tris-Cl, pH 6.8 containing 0.80 mL glycerol, 1.6 mL 10% (w/v) SDS, 0.4 mL β-mercaptoethanol, 0.2 mL 0.05% Bromophenol blue) was then added and diluted further if necessary. FIG. 5 shows expression of the wild type *E. corrodens* lysine decarboxylase in the *E. coli* pellets from IPTG induced cultures. There was no expression of this protein if the cultures were not induced with IPTG. The recombinant lysine decarboxylase (SEQ ID NO:4) encoded by SEQ ID NO:3 (the "optimized" version of the gene) had the same molecular weight (80 kDa) as native lysine decarboxylase (SEQ ID NO:2).

Enhanced Expression of *E. corrodens* Mutant Lysine Decarboxylase in *E. coli*.

Figure 6:
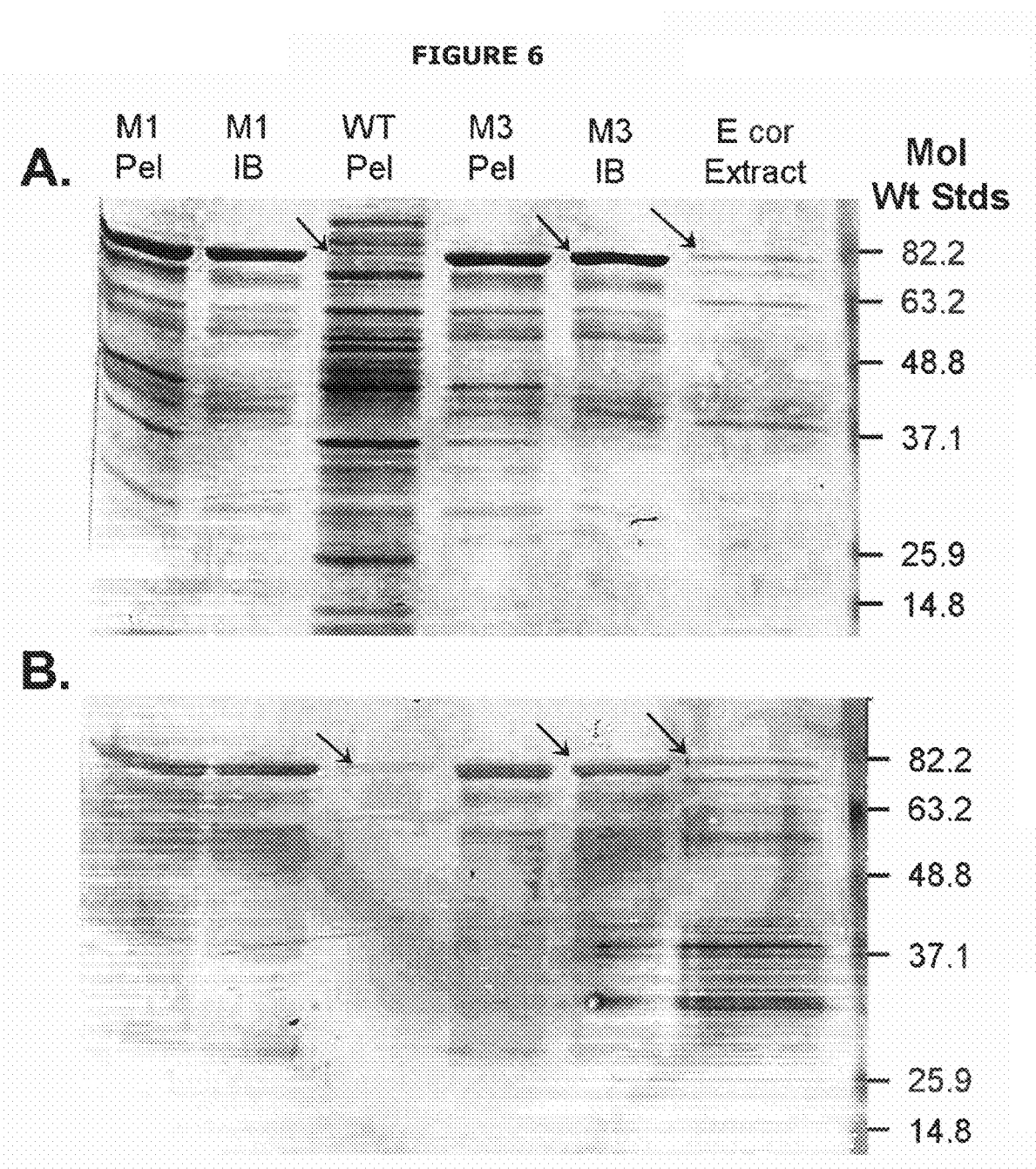
FIG. 6 shows blots of the isolated pellets from two mutants (M1 and M3 corresponding to mut1 and mut3 in FIG. 5. Top: Protein stained blot. Bottom: Western immunoblotted with immune goat serum diluted 1 to 25,000 as in FIG. 5. Pel indicates the same preparations added to the lanes as in FIG. 5; IB indicates the isolated inclusion body (5.0 µg protein added to each lane in 10 µL). *E. corrodens* extract (Ecor; 5 µg protein) was added as in FIG. 5. Arrows indicate the position of lysine decarboxylase.

Enhanced expression of a mutant version of the *E. coli* optimized lysine decarboxylase gene (SEQ ID NO:5) was used to produce a catalytically inactive protein mutant (K365→A365) having SEQ ID NO:6. This mutant protein was made from the original plasmid insert using a double stranded nucleotide primer with DNA PolI (StratageneQuickchange Kit). *E. coli* cells (100 µl) were transformed with pET11a containing the wild type or mutant gene. Following overnight growth on LB agar containing 100 µg/ml ampicillin (LB-amp), colonies were picked, expanded and lysed as described for the wild type lysine decarboxylase. FIG. 6 shows a plot of the purified, isolated inclusion bodies from two separately obtained mutant clones.

Poor expression of the wild type enzyme (SEQ ID NO:4) and strong expression of the mutant (SEQ ID NO:6) were observed in each of three clones separately obtained from the wild type (FIG. 5). Non-induced *E. coli* or *E. coli* transformed with pET11a without the gene did not express enzyme.

The transformed *E. coli* may express the wild type *E. corrodens* lysine decarboxylase poorly because of its removal of lysine from the cytosol restricting *E. coli* strains to those expressing a minimal amount of enzyme. Although this restriction should not apply to an enzyme-inactive mutant, all position 365 mutants encoding an amino acid at position 365 other than alanine expressed minimal protein like the wild type, or none at all.

Purification of the Lysine Decarboxylase Mutant Inclusion Body.

Briefly, 50 mL of the cell culture of *E. coli* expressing the recombinant lysine decarboxylase mutant (SEQ ID NO:6) was centrifuged at 10,000 rpm at 4° C. for 10 minutes. The pellet was suspended in 6 mL of 25 mM tris, pH 8.0, re-centrifuged and the weight of the *E. coli* pellet determined; typically it was 0.2-0.4 g. The pellet was resuspended in 1 ml of cell lysis buffer I (50 mM Tris-Cl pH 8.0, 1 mM EDTA pH 8.0, 100 mM NaCl) by gentle vortexing. Pefabloc SC (1.4 µl of 100 mM) and lysozyme (5.67 µL of 50 mg/ml) were added and the suspension was stirred for 20 minutes at room temperature, after which 2 ml of deoxycholic acid (1 mg/mL) was added while still stirring. The suspension was then placed in a incubator at 30° and gently shaken. When the lysate became viscous, 2-4 µl of DNase I was added in 20 mM tris HCl pH 7.8 (1 mg/ml per g of *E. coli*) and the lysate was rocked at room temperature until no longer viscous (~30 minutes). The lysate was then centrifuged at 13,000 rpm for 15 minutes. The supernatant was removed and the purified pellet was frozen at −80° overnight.

Isolation of Mutant Lysine Decarboxylase Inclusion Body.

The pellet was resuspended in 9 volumes of cell lysis buffer II (50 mM Tris-Cl pH 8.0, 10 mM EDTA pH 8.0, 100 mM NaCl, 0.50% v/v Triton X-100) at 4° C. and transferred into a 30 mL glass centrifuge tube. After incubation for 5 minutes at room temperature the suspension was centrifuged at 10,000 rpm for 15 minutes at 4° C. The pellet was then resuspended in approximately 300 μL of distilled water, centrifuged for 10 minutes at 4° C. and the supernatant discarded. The pellet was resuspended in 50 μL of lysis buffer II. Lysozyme (1 uL of 50 mg/mL) was immediately added and the suspension was incubated at room temperature for 15 minutes. After centrifugation at 4° for 2 minutes, the supernatant was discarded and the pellet resuspended in 1 mL of Cell Lysis Buffer II. The suspension was transferred to a pre-weighed microcentrifuge tube and centrifuged at 4° for 2 minutes at 14,000 rpm. The supernatant was decanted and the resuspension in Cell Lysis Buffer II was repeated twice more without adding Lysozyme and then twice more with enough distilled water to make a 1 mg/ml suspension. The major protein in the inclusion body was the protein of 80 kDal corresponding in size to the native $E.$ $corrodens$ protein (FIG. 6).

Example IV

Isolated Mutant Lysine Decarboxylase Inclusion Body Induces Lysine Decarboxylase Inhibiting Antibodies in Rabbits The mutant lysine decarboxylase inclusion body (0.2 mg protein/ml) was mixed with Rehydragel like the $E.$ $corrodens$ lysine decarboxylase and given subcutaneously at days 0, 21 and 42 to each of 2 rabbits as described above for dogs. The results (FIG. 7) are comparable with FIG. 4B if day −77 is adjusted to day 0, but the inhibition was not as strong or as long lasting. Given that different species and different antigen preparations were used, the results are sufficiently similar to indicate that antibodies obtained by immunizing with the mutant lysine decarboxylase inclusion body inhibit lysine decarboxylase activity. The recombinant, mutated lysine decarboxylase, or some variant, thereof that induces antibodies that inhibit native $E.$ $corrodens$ lysine decarboxylase activity, is therefore contemplated herein as the novel vaccine composition of the present disclosure.

REHYDRAGEL®, adjuvant gave strong but short-lived immunity. By way of non-limiting examples, other commercially acceptable adjuvants for vaccines are: CARBIGEN™ POLYGEN™ and EMULSIGEN®. These adjuvants may be purchased from MVP Laboratories Inc., 4805 G St., Omaha Nebr. 68117, USA and may be used alone or mixed with Rehydragel and other adjuvants in the vaccine. Detailed instructions are available herein.

CARBIGEN™ is an adjuvant suspension containing a proprietary emulsified component and is free of animal-origin ingredients. It contains Carbapol 934P, a pharmacological grade, cross-linking polymer that encapsulates the antigen, providing slow release and depot effects. This combination improves the presentation of antigen to effector cells and provides a significant enhancement of the immune response and vaccine efficacy. Using a sterile beaker and stir bar, the inclusion body containing the K-A mutant protein was diluted to contain 0.2 mg/ml in sterile phosphate buffered saline, 0.01% phenol red and 10% of the purchased Carbigen solution. The Carbigen suspension is stirred gently at room temperature and the pH is acidic, as indicated by the yellow color of the phenol red dye. The antigen becomes encapsulated and after 4 h, the reaction is stopped by adding 10 M NaOH to pH 6.8-7.2 (phenol red dye turns bright orange). The mixture was left overnight stirring gently at room temperature and the pH checked again but adjustment was unnecessary. The suspension was then dispensed in sterile vials in 1.0 ml aliquots for immunization.

POLYGEN™ is a low molecular weight copolymer adjuvant that forms cross-links in solution to form a high molecular weight gel. A POLYGEN™ suspension was prepared by diluting the purchased solution 1 to 7 such that the antigen concentration in the gel was 0.2 mg/mL. EMULSIGEN®-P is a sterile oil-in water emulsion containing uniformly dispersed micron-sized oil droplets that increase the surface area available to vaccines. An EMULSIGEN®-P suspension was prepared by diluting the purchased solution 1 to 5 such that the antigen concentration was 0.2 mg/mL.

Utility

The present invention in one embodiment is directed to a vaccine for inducing an antibody response against the lysine decarboxylase from $E.$ $corrodens$, the vaccine thus comprising an entire lysine decarboxylase mutant protein, or immunogenic portions thereof. In a preferred embodiment of the invention, the vaccine and method prevents or ameliorates gingivitis and chronic periodontitis in humans or animal subjects. In one method of the invention, an inclusion body comprising the isolated mutant lysine decarboxylase is administered as a vaccine composition to the subject as described below. The vaccine preferably comprises a pharmacologically acceptable carrier and optionally an adjuvant and induces an immunogenic response effective against lysine decarboxylase in vivo.

As used herein, the term "immunogenic or immunogenically active" designates the ability to stimulate an immune response that causes the production of circulating or secretory antibodies in blood plasma or salivary or other secretions entering the oral cavity. These antibodies react with $E.$ $corrodens$ lysine decarboxylase protein and inhibit or mitigate its enzymatic activity.

As used herein the term "adjuvant" refers to any component, which improves the body's response to a vaccine. The adjuvant will typically comprise about 0.1 to 50% vol/vol of the vaccine formulation of the invention, more preferably about 1 to 50% of the vaccine, and even more desirably about 1 to 20% thereof. Amounts of about 4 to 10% may be even more preferred. Adjuvants are well known in the art thus further description thereof herein is not deemed necessary.

At least one dosage unit per subject is contemplated herein as a vaccination regimen. In some embodiments, two or more dosage units may be especially useful. By way of non-limiting example, dosage unit of the $E.$ $corrodens$ lysine decarboxylase protein, or of the recombinant lysine decarboxylase mutant inclusion body from $E.$ $coli$, is typically in the range of 0.01 mg to 1 mg and more preferably is in the range of 0.1-0.3 mg. As noted elsewhere herein, the protein is usually given in a suspension with adjuvant. The skilled artisan will quickly recognize that a particular quantity of vaccine composition per dosage unit, as well as the total number of dosage units per vaccination regimen, may be optimized, so long as an effective immunizing amount of the protein or a component thereof is ultimately delivered to the subject.

Other components of the vaccine composition may include wetting or dispersing agents in amounts of between 0.1 to 0.25%, more preferably 1 to 10% and even more preferably about 1-3% by volume. Such useful non-ionic surfactants include polyoxyethylene/polyoxypropylene block copolymers, especially those marketed under the trademark PLURONIC® and available from BASF Corporation (Mt Olive N.J.). Other useful nonionic surfactants include polyoxyethylene esters such as polyoxyethylene sorbitan monooleate, available under the trademark TWEEN 80®. It may be desirable to include more than one, e.g., at least two, wetting or dispersing agents in the adjuvant as part of the vaccine composition of the invention.

Other components of the adjuvant may include such preservative compounds as formalin and thimerosal in amounts of up to about 1% vol/vol of the adjuvant.

Pharmacologically acceptable carriers suitable for use in the vaccine composition of the invention may be any conventional liquid carrier suitable for pharmaceutical compositions, preferably a balanced salt solution, physiological saline, or other water-based solution suitable for use in tissue culture media. Other available carriers well known to those of ordinary skill in the art may also be utilized.

Additional excipients available and known to those of ordinary skill in the art may also be included in the vaccine composition according to the various embodiments heretofore described. For example, pH modifiers may be utilized.

In a preferred embodiment of the invention, the novel vaccine composition contemplated herein may be formulated in a dosage unit form as heretofore described to facilitate administration and ensure uniformity of dosage. Formulation may be effected using available techniques, such as those applicable to preparations of emulsions.

The novel vaccine composition contemplated herein may be administered parenterally, intramuscularly, subcutaneously, intraperitoneally, intradermally, orally, or intranasally. By way of non-limiting example, a dosage unit will typically be 1.0 mL±0.5 mL of vaccine composition.

The vaccines contemplated herein, as noted, may be utilized in connection with animals (i.e., domestic or non-domestic), as well as humans, as animals experience many of the same dental conditions as humans. The subjects which may be treated with the novel vaccine contemplated herein include, but are not limited to, mammals, including primates such as humans, chimpanzees, baboons, gorillas and orangutans, monkeys and lemurs; mustelids including minks; camelids, including camels, llamas, alpacas, and vicunas; felids including lions, tigers and domestic cats; canids including dogs; bovids including cattle; equids including horses; ovids including sheep and goats; suids including pigs; and cervids including deer, elk and moose.

Each of U.S. Pat. Nos. 6,103,220; 6,187,296; 6,576,435; and 6,974,700, U.S. Published Application 2008/0213305, as well as all other published applications, articles, or books cited herein, are expressly incorporated herein by reference in their entirety.

The present invention is not to be limited in scope by the specific embodiments described herein, since such embodiments are intended as but single illustrations of one aspect of the invention and any functionally equivalent embodiments are within the scope of this invention. Indeed, various modifications of the methods and compositions of the invention in addition to those shown and described herein will become apparent to those skilled in the art from the foregoing description.

REFERENCES

1. Hatakeyama S, Yaegashi T. Oikawa Y et al. Expression pattern of adhesion molecules in junctional epithelium differs from that in other gingival epithelia. J Periodontal Res 2006; 41(4):322-328.

2. Salonen J I. Proliferative potential of the attached cells of human junctional epithelium. J Periodontal Res 1994; 29(1): 41-45.

3. Levine M, Progulske-Fox A, Denslow N D et al. Identification of lysine decarboxylase as a mammalian cell growth inhibitor in *Eikenella corrodens*: possible role in periodontal disease. Microb Pathog 2001; 30(4):179-192.

4. Trombelli L, Tatakis D N, Scapoli C, Bottega S, Orlandini E, Tosi M. Modulation of clinical expression of plaque-induced gingivitis. II. Identification of "high-responder" and "low-responder" subjects. J Clin Periodontol 2004; 31(4): 239-252.

5. Li J, Helmerhorst E J, Leone C W et al. Identification of early microbial colonizers in human dental biofilm. J Appl Microbiol 2004; 97(6):1311-1318.

6. Ramberg P, Sekino S, Uzel N G, Socransky S, Lindhe J. Bacterial colonization during de novo plaque formation. J Clin Periodontol 2003; 30(11):990-995.

7. Loe H, Holm-Pedersen P. Absence and presence of fluid from normal and inflamed gingivae. Periodontics 1965; 3:171-177.

8. Marsh P D. Are dental diseases examples of ecological catastrophes? Microbiology 2003; 149(Pt 2):279-294.

9. Socransky S S, Haffajee A D. Periodontal microbial ecology. Periodontol 2000 2005; 38:135-187.

10. Listgarten M A. Pathogenesis of periodontitis. J Clin Periodontol 1986; 13(5):418-430.

11. Hardham J, Dreier K, Wong 1, Sfintescu C, Evans R T. Pigmented-anaerobic bacteria associated with canine periodontitis. Vet Microbiol 2005; 106(1-2):119-128.

12. Hardham J, Reed M, Wong J et al. Evaluation of a monovalent companion animal periodontal disease vaccine in an experimental mouse periodontitis model. Vaccine 2005; 23(24):3148-3156.

13. Lindhe J, Hamp S E, Loe H. Plaque induced periodontal disease in beagle dogs. A 4-year clinical, roentgenographical and histometrical study. J Periodontal Res 1975; 10(5): 243-255.

14. Paquette D W, Waters G S, Stefanidou V L et al. Inhibition of experimental gingivitis in beagle dogs with topical salivary histatins. J Clin Periodontol 1997; 24(4):216-222.

What is claimed is:

1. An isolated lysine decarboxylase mutant comprising a substitution at a position corresponding to position 365 of SEQ ID NO:2, wherein said mutant has at least 95% sequence identity to SEQ ID NO:2 and has diminished lysine decarboxylase activity, wherein the mutant is able to stimulate an immune response against lysine decarboxylase.

2. An isolated polypeptide having at least 95% amino acid sequence identity to the amino acid sequence of the polypeptide having SEQ ID NO:2, the isolated polypeptide having an amino acid substitution corresponding to position 365 of SEQ ID NO:2, wherein the isolated polypeptide having the amino acid substitution corresponding to position 365 of SEQ ID NO:2 is able to stimulate an immune response against lysine decarboxylase.

3. The isolated mutant of claim 1 comprising SEQ ID NO:6.

4. An isolated polypeptide having at least 95% amino acid sequence identity to the amino acid sequence of the polypeptide having SEQ ID NO:2, the isolated polypeptide having an amino acid substitution corresponding to position 365 of SEQ ID NO:2.

5. The isolated polypeptide of claim 4 wherein the amino acid substitution comprises alanine in place of lysine.

6. The isolated polypeptide of claim 4 having at least 99% amino acid sequence identity to the amino acid sequence of the polypeptide of SEQ ID NO:2.

7. A purified inclusion body produced recombinantly in *E. coli*, the inclusion body comprising the isolated polypeptide of claim 4.

8. A vaccine composition comprising the isolated polypeptide of claim 1, the polypeptide is able to stimulate an immune response against lysine decarboxylase.

9. The vaccine composition of claim 8 comprising a pharmaceutically-acceptable carrier or vehicle.

10. The vaccine composition of claim 8 further comprising an adjuvant.

11. A method of treating or inhibiting periodontal disease in a subject by inducing an immunogenic response against lysine decarboxylase, comprising:

providing the vaccine composition of claim 8; and administering the vaccine composition to the subject.

* * * * *

UNITED STATES PATENT AND TRADEMARK OFFICE
CERTIFICATE OF CORRECTION

| | | |
|---|---|---|
| PATENT NO. | : 7,794,726 B2 | Page 1 of 1 |
| APPLICATION NO. | : 12/329327 | |
| DATED | : September 14, 2010 | |
| INVENTOR(S) | : Martin Levine | |

It is certified that error appears in the above-identified patent and that said Letters Patent is hereby corrected as shown below:

In the Specification:
Column 20, line 4: Delete "Wong 1," and replace with -- Wong J, --.

Signed and Sealed this
Twenty-second Day of February, 2011

David J. Kappos
*Director of the United States Patent and Trademark Office*

SEQUENCE LISTING

<160> NUMBER OF SEQ ID NOS: 6

<210> SEQ ID NO 1
<211> LENGTH: 2130
<212> TYPE: DNA
<213> ORGANISM: Eikenella corrodens

<400> SEQUENCE: 1

```
atgaagaaca tcttattagg ctgtggtcat aaggaacttg gtgactatct gaagagcttg        60
attgaaactt tggaaaaggg tggtcacacc atccgaatag cccatgaccc gcaagaaatc       120
ctgacgttcc tgaaacatga cgccagaata ggctcagtgc tttgtacact ggatattttc       180
aaccgagaat tagacgaaca aattattgca ctcaacgatg agctacccgt attcattctg       240
aagcccaccg actgcgacaa acccgtggac ttcggcgctg taggcgacca tgccaccttc       300
atcgattgcc atctgttcag caacgaagac gttgttgata aaattgaaaa agcaatctgt       360
cactatatcg caaatatcac cccgcccttc actaaagccc tgtttgacta cgttgataaa       420
aacaaataca cattctgtac tccgggtcac atgagcggta ccgcttttct gaaatctccc       480
gtaggtagcc tgttctacga cttctacggt gaaaacacat tcaaatcaga tatttcagtt       540
tctatgggcg aattgggctc tctgctcgac cactccggcc gcacaaaga ggccgaagaa        600
tacatcgccg aaaccttcaa tgccgaccac agctacatcg taaccaacgg tacttccacc       660
gccaacaaaa tcgtgggtat gtactccgtt ccggccggca gcaccgtact gatcgaccgt       720
aactgccaca atcattaac ccacctgttg atgatgagcg acattactcc ggtgtatctg        780
aaaccgaccc gtaacgccta cggtatcttg ggtggtattc cgcaaaaaga attcaccaaa       840
gaagttatta ccgaaaaact taccaaagtt ccgggcgcca cttggccggt acatgccgtg       900
attaccaact ccacttatga cggcctgttc tacaacaccg acaagatcaa agacaccctg       960
gatgtgaaat ccatccactt cgactctgct tgggttccct acaccaactt cagcccgatc      1020
tacaacggca aaccggtat gggcggtaag caggttaaag acaaggtaat ctttgaaacc       1080
cactctaccc acaaactgct ggccgcattc tcacaggctt ccatgattca cgttaagggt      1140
aacctgaaca ccgccaccct cggcgaagcc tacatgatgc acacctccac ttctccgttc      1200
taccccatgg tagcctctac tgaagtggca gcagccatga tgcgcggcaa ctccggtaaa      1260
cgcctgatgc aggattcact ggaacgcgcc gttaaattcc gtaaggaaat caagaaacac      1320
aaagcccatg ccgactcatg gtatttcgat gtatggcaac ctgaaaatgt tgacaacatc      1380
gaatgctggg aattgcatca gaccgacaaa tggcacggct caaagacat cgacgcccag       1440
cacatgtacc tcgacccgat taaggtaact ctgcttaccc cgggcttgga taaaaacggc      1500
gagctggaaa aaaccggtat ccccgccaac ctcgtttcca aattcttgga agaccgcggc      1560
atcatcgtgg agaaaaccgg ccctacaac atcctcgtgc tcttcagcat cggcgtggac       1620
gacaccaaag ccctcagcct gctgcacgca ttgaacgagt tcaaatccct gtacgatgcc      1680
aacgccaccg tagaagaagt attgccgcgc gtattcaacg aatcgccctc tttctaccaa      1740
gaaatgcgga ttcaagaatt ggcacaaggc atccacagct gatctgcaa acacaacctg       1800
cctgaactga tgttcagcgc attcgaagtg ttgccgacca tggtgatgaa cccgcacaaa      1860
gccttccagc ttgagctgaa aggtcagatt gaagactgct acttggaaga catggtaggc      1920
aagatcaacg ccaacatgat tctgccctat cctcccggcg taccgttggt aatgcctggt      1980
gaaatgatca ccgaagaaag caagcccatc ttggaattcc tgatgatgct gtgcgaaatc      2040
ggcgccccact tccccggctt cgaaaccgac atccacggtg cttaccgtca agaagacggc      2100
cgctataaag ttaagattgt taaagcttaa                                        2130
```

<210> SEQ ID NO 2
<211> LENGTH: 709
<212> TYPE: PRT
<213> ORGANISM: Eikenella corrodens

```
<400> SEQUENCE: 2

Met Lys Asn Ile Leu Leu Gly Cys Gly His Lys Glu Leu Gly Asp Tyr
1               5                   10                  15

Leu Lys Ser Leu Ile Glu Thr Leu Glu Lys Gly Gly His Thr Ile Arg
            20                  25                  30

Ile Ala His Asp Pro Gln Glu Ile Leu Thr Phe Leu Lys His Asp Ala
        35                  40                  45

Arg Ile Gly Ser Val Leu Cys Thr Leu Asp Ile Phe Asn Arg Glu Leu
    50                  55                  60

Asp Glu Gln Ile Ile Ala Leu Asn Asp Glu Leu Pro Val Phe Ile Leu
65                  70                  75                  80

Lys Pro Thr Asp Cys Asp Lys Pro Val Asp Phe Gly Ala Val Gly Asp
                85                  90                  95

His Ala Thr Phe Ile Asp Cys His Leu Phe Ser Asn Glu Asp Val Val
            100                 105                 110

Asp Lys Ile Glu Lys Ala Ile Cys His Tyr Ile Asp Asn Ile Thr Pro
        115                 120                 125

Pro Phe Thr Lys Ala Leu Phe Asp Tyr Val Asp Lys Asn Lys Tyr Thr
    130                 135                 140

Phe Cys Thr Pro Gly His Met Ser Gly Thr Ala Phe Leu Lys Ser Pro
145                 150                 155                 160

Val Gly Ser Leu Phe Tyr Asp Phe Tyr Gly Glu Asn Thr Phe Lys Ser
                165                 170                 175

Asp Ile Ser Val Ser Met Gly Glu Leu Gly Ser Leu Leu Asp His Ser
            180                 185                 190

Gly Pro His Lys Glu Ala Glu Gly Tyr Ile Ala Glu Thr Phe Asn Ala
        195                 200                 205

Asp His Ser Tyr Ile Val Thr Asn Gly Thr Ser Thr Ala Asn Lys Ile
    210                 215                 220

Val Gly Met Tyr Ser Val Pro Ala Gly Ser Thr Val Leu Ile Asp Arg
225                 230                 235                 240

Asn Cys His Lys Ser Leu Thr His Leu Leu Met Met Ser Asp Ile Thr
                245                 250                 255

Pro Val Tyr Leu Lys Pro Thr Arg Asn Ala Tyr Gly Ile Leu Gly Gly
            260                 265                 270

Ile Pro Gln Lys Glu Phe Thr Lys Glu Val Ile Thr Glu Lys Leu Thr
        275                 280                 285

Lys Val Pro Gly Ala Thr Trp Pro Val His Ala Val Ile Thr Asn Ser
    290                 295                 300

Thr Tyr Asp Gly Leu Phe Tyr Asn Thr Asp Lys Ile Lys Asp Thr Leu
305                 310                 315                 320

Asp Val Lys Ser Ile His Phe Asp Ser Ala Trp Val Pro Tyr Thr Asn
                325                 330                 335

Phe Ser Pro Ile Tyr Asn Gly Lys Thr Gly Met Gly Gly Lys Gln Val
            340                 345                 350

Lys Asp Lys Val Ile Phe Glu Thr His Ser Thr His Lys Leu Leu Ala
        355                 360                 365

Ala Phe Ser Gln Ala Ser Met Ile His Val Lys Gly Asn Leu Asn Thr
    370                 375                 380

Ala Thr Phe Gly Glu Ala Tyr Met Met His Thr Ser Thr Ser Pro Phe
385                 390                 395                 400

Tyr Pro Met Val Ala Ser Thr Glu Val Ala Ala Ala Met Met Arg Gly
```

```
                    405                 410                 415
Asn Ser Gly Lys Arg Leu Met Gln Asp Ser Leu Glu Arg Ala Val Lys
            420                 425                 430

Phe Arg Lys Glu Ile Lys Lys His Lys Ala His Ala Asp Ser Trp Tyr
        435                 440                 445

Phe Asp Val Trp Gln Pro Glu Asn Val Asp Asn Ile Glu Cys Trp Glu
    450                 455                 460

Leu His Gln Thr Asp Lys Trp His Gly Phe Lys Asp Ile Asp Ala Gln
465                 470                 475                 480

His Met Tyr Leu Asp Pro Ile Lys Val Thr Leu Leu Thr Pro Gly Leu
                485                 490                 495

Asp Lys Asn Gly Glu Leu Glu Lys Thr Gly Ile Pro Ala Asn Leu Val
            500                 505                 510

Ser Lys Phe Leu Glu Asp Arg Gly Ile Ile Val Glu Lys Thr Gly Pro
        515                 520                 525

Tyr Asn Ile Leu Val Leu Phe Ser Ile Gly Val Asp Asp Thr Lys Ala
    530                 535                 540

Leu Ser Leu Leu His Ala Leu Asn Glu Phe Lys Ser Leu Tyr Asp Ala
545                 550                 555                 560

Asn Ala Thr Val Glu Glu Val Leu Pro Arg Val Phe Asn Glu Ser Pro
                565                 570                 575

Ser Phe Tyr Gln Glu Met Arg Ile Gln Glu Leu Ala Gln Gly Ile His
            580                 585                 590

Ser Leu Ile Cys Lys His Asn Leu Pro Glu Leu Met Phe Ser Ala Phe
        595                 600                 605

Glu Val Leu Pro Thr Met Val Met Asn Pro His Lys Ala Phe Gln Leu
    610                 615                 620

Glu Leu Lys Gly Gln Ile Glu Asp Cys Tyr Leu Glu Asp Met Val Gly
625                 630                 635                 640

Lys Ile Asn Ala Asn Met Ile Leu Pro Tyr Pro Pro Gly Val Pro Leu
                645                 650                 655

Val Met Pro Gly Glu Met Ile Thr Glu Glu Ser Lys Pro Ile Leu Glu
            660                 665                 670

Phe Leu Met Met Leu Cys Glu Ile Gly Ala His Phe Pro Gly Phe Glu
        675                 680                 685

Thr Asp Ile His Gly Ala Tyr Arg Gln Glu Asp Gly Arg Tyr Lys Val
    690                 695                 700

Lys Ile Val Lys Ala
705

<210> SEQ ID NO 3
<211> LENGTH: 2130
<212> TYPE: DNA
<213> ORGANISM: Artificial sequence
<220> FEATURE:
<223> OTHER INFORMATION: Artificially synthesized.

<400> SEQUENCE: 3
atgaaaaaca ttctgctggg ttgcggtcat aaagaactgg gcgactatct gaaatcactg      60
atcgaaaccc tggaaaaagg cggccatacg attcgcattg cacacgatcc gcaagaaatt     120
ctgaccttcc tgaaacacga tgcacgcatt ggttctgtcc tgtgtaccct ggatattttt     180
aatcgtgaac tggacgaaca gattatcgcg ctgaatgacg aactgccggt tttcattctg     240
aaaccgacgg attgcgataa accggtggat ttcggtgcgg tgggcgatca tgccacgttt     300
```

-continued

| | |
|---|---|
| atcgattgtc atctgttttc caacgaagac gtcgtcgata aaatcgaaaa agccatctgc | 360 |
| cactacatcg ataacattac gccgccgttc accaaagcac tgtttgacta cgtggataaa | 420 |
| aataaatata ccttttgcac cccgggccac atgagcggta ccgcgtttct gaaatcaccg | 480 |
| gtcggttctc tgttctacga cttctacggc gaaaacacct taaatcaga catttctgtg | 540 |
| agcatgggcg aactgggcag cctgctggac cacagcggcc cgcacaaaga agcagaagaa | 600 |
| tatatcgcag aaacgtttaa cgcggatcat agctacattg tgaccaacgg tacgagcacc | 660 |
| gccaataaaa ttgtgggcat gtatagcgtg ccggccggca gcaccgtcct gatcgaccgc | 720 |
| aactgtcata aagcctgac gcatctgctg atgatgtcag atattacccc ggtgtacctg | 780 |
| aaaccgacgc gtaatgcgta tggcattctg ggtggcattc cgcagaaaga atttaccaaa | 840 |
| gaagtgatta cggaaaaact gaccaaagtg ccgggcgcga cctggccggt gcatgcagtg | 900 |
| attaccaaca gcacctacga cggtctgttt tacaacaccg ataaaatcaa agacaccctg | 960 |
| gatgttaaat ctattcattt cgactctgcg tgggtcccgt ataccaactt ttctccgatc | 1020 |
| tataatggta aaccggtat gggcggcaaa caggttaaag acaaagtcat tttcgaaacc | 1080 |
| cactcaaccc acaaactgct ggcagcattc tctcaggcat caatgattca cgtgaaaggt | 1140 |
| aacctgaaca cggcgaccct cggtgaagcc tatatgatgc ataccagcac gagcccgttc | 1200 |
| tatccgatgg tcgcgagcac ggaagttgct gctgcgatga tgcgtggtaa cagtggtaaa | 1260 |
| cgcctgatgc aggactcgct ggaacgcgcg gttaaatttc gtaaagaaat caaaaaacat | 1320 |
| aaagcccatg cagattcatg gtactttgac gtgtggcagc cggaaaatgt cgataatatt | 1380 |
| gaatgctggg aactgcatca aacggataaa tggcatggtt caaagatat tgatgcgcag | 1440 |
| cacatgtacc tggacccgat caaagtgacc ctgctgaccc cgggtctgga taaaaatggc | 1500 |
| gaactggaaa aaccggtat tccggctaac ctggtgtcta aatttctgga agatcgtggc | 1560 |
| attattgtgg aaaaaacggg tccgtataac attctggtgc tgtttagcat tggcgtggat | 1620 |
| gataccaaag cactgtcact gctgcatgct ctgaatgaat tcaaaagcct gtatgatgcg | 1680 |
| aacgcaaccg ttgaagaagt gctgccgcgt gtgttcaacg aaagcccgag tttttatcag | 1740 |
| gaaatgcgta ttcaggaact ggcacagggc atccacagcc tgatttgcaa acataacctg | 1800 |
| ccggaactga tgttcagtgc gtttgaagtg ctgccgacga tggttatgaa tccgcacaaa | 1860 |
| gcctttcagc tggaactgaa aggtcagatc gaagattgct atctggaaga tatggttggt | 1920 |
| aaaattaacg caaatatgat tctgccgtat ccgccgggcg tcccgctggt gatgccgggt | 1980 |
| gaaatgatca cggaagaatc caaaccgatt ctggaatttc tgatgatgct gtgcgaaatc | 2040 |
| ggcgcgcatt ttccgggctt tgaaaccgat attcacggtg cataccgtca ggaagatggc | 2100 |
| cgctacaaag tcaaaattgt gaaagcctaa | 2130 |

<210> SEQ ID NO 4
<211> LENGTH: 709
<212> TYPE: PRT
<213> ORGANISM: Artificial sequence
<220> FEATURE:
<223> OTHER INFORMATION: Artificially synthesized.

<400> SEQUENCE: 4

Met Lys Asn Ile Leu Leu Gly Cys Gly His Lys Glu Leu Gly Asp Tyr
1               5                   10                  15

Leu Lys Ser Leu Ile Glu Thr Leu Glu Lys Gly Gly His Thr Ile Arg
            20                  25                  30

Ile Ala His Asp Pro Gln Glu Ile Leu Thr Phe Leu Lys His Asp Ala

```
            35                  40                  45
Arg Ile Gly Ser Val Leu Cys Thr Leu Asp Ile Phe Asn Arg Glu Leu
 50                  55                  60

Asp Glu Gln Ile Ile Ala Leu Asn Asp Glu Leu Pro Val Phe Ile Leu
 65                  70                  75                  80

Lys Pro Thr Asp Cys Asp Lys Pro Val Asp Phe Gly Ala Val Gly Asp
                 85                  90                  95

His Ala Thr Phe Ile Asp Cys His Leu Phe Ser Asn Glu Asp Val Val
                100                 105                 110

Asp Lys Ile Glu Lys Ala Ile Cys His Tyr Ile Asp Asn Ile Thr Pro
                115                 120                 125

Pro Phe Thr Lys Ala Leu Phe Asp Tyr Val Asp Lys Asn Lys Tyr Thr
130                 135                 140

Phe Cys Thr Pro Gly His Met Ser Gly Thr Ala Phe Leu Lys Ser Pro
145                 150                 155                 160

Val Gly Ser Leu Phe Tyr Asp Phe Tyr Gly Glu Asn Thr Phe Lys Ser
                165                 170                 175

Asp Ile Ser Val Ser Met Gly Glu Leu Gly Ser Leu Leu Asp His Ser
                180                 185                 190

Gly Pro His Lys Glu Ala Glu Glu Tyr Ile Ala Glu Thr Phe Asn Ala
                195                 200                 205

Asp His Ser Tyr Ile Val Thr Asn Gly Thr Ser Thr Ala Asn Lys Ile
                210                 215                 220

Val Gly Met Tyr Ser Val Pro Ala Gly Ser Thr Val Leu Ile Asp Arg
225                 230                 235                 240

Asn Cys His Lys Ser Leu Thr His Leu Leu Met Met Ser Asp Ile Thr
                245                 250                 255

Pro Val Tyr Leu Lys Pro Thr Arg Asn Ala Tyr Gly Ile Leu Gly Gly
                260                 265                 270

Ile Pro Gln Lys Glu Phe Thr Lys Glu Val Ile Thr Glu Lys Leu Thr
                275                 280                 285

Lys Val Pro Gly Ala Thr Trp Pro Val His Ala Val Ile Thr Asn Ser
290                 295                 300

Thr Tyr Asp Gly Leu Phe Tyr Asn Thr Asp Lys Ile Lys Asp Thr Leu
305                 310                 315                 320

Asp Val Lys Ser Ile His Phe Asp Ser Ala Trp Val Pro Tyr Thr Asn
                325                 330                 335

Phe Ser Pro Ile Tyr Asn Gly Lys Thr Gly Met Gly Gly Lys Gln Val
                340                 345                 350

Lys Asp Lys Val Ile Phe Glu Thr His Ser Thr His Lys Leu Leu Ala
                355                 360                 365

Ala Phe Ser Gln Ala Ser Met Ile His Val Lys Gly Asn Leu Asn Thr
                370                 375                 380

Ala Thr Phe Gly Glu Ala Tyr Met Met His Thr Ser Thr Ser Pro Phe
385                 390                 395                 400

Tyr Pro Met Val Ala Ser Thr Glu Val Ala Ala Ala Met Met Arg Gly
                405                 410                 415

Asn Ser Gly Lys Arg Leu Met Gln Asp Ser Leu Glu Arg Ala Val Lys
                420                 425                 430

Phe Arg Lys Glu Ile Lys Lys His Lys Ala His Ala Asp Ser Trp Tyr
                435                 440                 445

Phe Asp Val Trp Gln Pro Glu Asn Val Asp Asn Ile Glu Cys Trp Glu
450                 455                 460
```

```
Leu His Gln Thr Asp Lys Trp His Gly Phe Lys Asp Ile Asp Ala Gln
465                 470                 475                 480

His Met Tyr Leu Asp Pro Ile Lys Val Thr Leu Leu Thr Pro Gly Leu
                485                 490                 495

Asp Lys Asn Gly Glu Leu Glu Lys Thr Gly Ile Pro Ala Asn Leu Val
            500                 505                 510

Ser Lys Phe Leu Glu Asp Arg Gly Ile Ile Val Glu Lys Thr Gly Pro
        515                 520                 525

Tyr Asn Ile Leu Val Leu Phe Ser Ile Gly Val Asp Asp Thr Lys Ala
    530                 535                 540

Leu Ser Leu Leu His Ala Leu Asn Glu Phe Lys Ser Leu Tyr Asp Ala
545                 550                 555                 560

Asn Ala Thr Val Glu Glu Val Leu Pro Arg Val Phe Asn Glu Ser Pro
                565                 570                 575

Ser Phe Tyr Gln Glu Met Arg Ile Gln Glu Leu Ala Gln Gly Ile His
            580                 585                 590

Ser Leu Ile Cys Lys His Asn Leu Pro Glu Leu Met Phe Ser Ala Phe
        595                 600                 605

Glu Val Leu Pro Thr Met Val Met Asn Pro His Lys Ala Phe Gln Leu
    610                 615                 620

Glu Leu Lys Gly Gln Ile Glu Asp Cys Tyr Leu Glu Asp Met Val Gly
625                 630                 635                 640

Lys Ile Asn Ala Asn Met Ile Leu Pro Tyr Pro Pro Gly Val Pro Leu
                645                 650                 655

Val Met Pro Gly Glu Met Ile Thr Glu Glu Ser Lys Pro Ile Leu Glu
            660                 665                 670

Phe Leu Met Met Leu Cys Glu Ile Gly Ala His Phe Pro Gly Phe Glu
        675                 680                 685

Thr Asp Ile His Gly Ala Tyr Arg Gln Glu Asp Gly Arg Tyr Lys Val
    690                 695                 700

Lys Ile Val Lys Ala
705

<210> SEQ ID NO 5
<211> LENGTH: 2130
<212> TYPE: DNA
<213> ORGANISM: Artificial sequence
<220> FEATURE:
<223> OTHER INFORMATION: Artificially synthesized.

<400> SEQUENCE: 5
atgaaaaaca ttctgctggg ttgcggtcat aaagaactgg cgactatctg gaaatcactg      60
atcgaaaccc tggaaaaagg cggccatacg attcgcattg cacacgatcc gcaagaaatt     120
ctgaccttcc tgaaacacga tgcacgcatt ggttctgtcc tgtgtaccct ggatattttt     180
aatcgtgaac tggacgaaca gattatcgcg ctgaatgacg aactgccggt tttcattctg     240
aaaccgacgg attgcgataa accggtggat ttcggtgcgg tgggcgatca tgccacgttt     300
atcgattgtc atctgttttc caacgaagac gtcgtcgata aaatcgaaaa agccatctgc     360
cactacatcg ataacattac gccgccgttc accaaagcac tgtttgacta cgtggataaa     420
aataaatata cctttttgcac cccgggccac atgagcggta ccgcgtttct gaaatcaccg     480
gtcggttctc tgttctacga cttctacggc gaaacacct ttaaatcaga catttctgtg     540
agcatgggcg aactgggcag cctgctggac cacagcggcc gcacaaaga agcagaagaa     600
```

-continued

```
tatatcgcag aaacgtttaa cgcggatcat agctacattg tgaccaacgg tacgagcacc      660
gccaataaaa ttgtgggcat gtatagcgtg ccggccggca gcaccgtcct gatcgaccgc      720
aactgtcata aaagcctgac gcatctgctg atgatgtcag atattacccc ggtgtacctg      780
aaaccgacgc gtaatgcgta tggcattctg ggtggcattc cgcagaaaga atttaccaaa      840
gaagtgatta cggaaaaact gaccaaagtg ccgggcgcga cctggccggt gcatgcagtg      900
attaccaaca gcacctacga cggtctgttt tacaacaccg ataaaatcaa agacaccctg      960
gatgttaaat ctattcattt cgactctgcg tgggtcccgt ataccaactt ttctccgatc     1020
tataatggta aaaccggtat gggcggcaaa caggttaaag acaaagtcat tttcgaaacc     1080
cactcaaccc acgcactgct ggcagcattc tctcaggcat caatgattca cgtgaaaggt     1140
aacctgaaca cggcgacctt cggtgaagcc tatatgatgc ataccagcac gagcccgttc     1200
tatccgatgg tcgcgagcac ggaagttgct gctgcgatga tgcgtggtaa cagtggtaaa     1260
cgcctgatgc aggactcgct ggaacgcgcg gttaaatttc gtaaagaaat caaaaaacat     1320
aaagcccatg cagattcatg gtactttgac gtgtggcagc cggaaaatgt cgataatatt     1380
gaatgctggg aactgcatca aacggataaa tggcatggtt tcaaagatat tgatgcgcag     1440
cacatgtacc tggacccgat caaagtgacc ctgctgaccc cgggtctgga taaaaatggc     1500
gaactggaaa aaccggtat tccggctaac ctggtgtcta aatttctgga agatcgtggc     1560
attattgtgg aaaaaacggg tccgtataac attctggtgc tgtttagcat tggcgtggat     1620
gataccaaag cactgtcact gctgcatgct ctgaatgaat tcaaaagcct gtatgatgcg     1680
aacgcaaccg ttgaagaagt gctgccgcgt gtgttcaacg aaagcccgag tttttatcag     1740
gaaatgcgta ttcaggaact ggcacagggc atccacagcc tgatttgcaa acataacctg     1800
ccggaactga tgttcagtgc gtttgaagtg ctgccgacga tggttatgaa tccgcacaaa     1860
gcctttcagc tggaactgaa aggtcagatc gaagattgct atctggaaga tatggttggt     1920
aaaattaacg caaatatgat tctgccgtat ccgccgggcg tcccgctggt gatgccgggt     1980
gaaatgatca cggaagaatc caaaccgatt ctggaatttc tgatgatgct gtgcgaaatc     2040
ggcgcgcatt ttccgggctt tgaaaccgat attcacggtg cataccgtca ggaagatggc     2100
cgctacaaag tcaaaattgt gaaagcctaa                                      2130
```

<210> SEQ ID NO 6
<211> LENGTH: 709
<212> TYPE: PRT
<213> ORGANISM: Artificial sequence
<220> FEATURE:
<223> OTHER INFORMATION: Artificially synthesized.

<400> SEQUENCE: 6

```
Met Lys Asn Ile Leu Leu Gly Cys Gly His Lys Glu Leu Gly Asp Tyr
1               5                   10                  15
Leu Lys Ser Leu Ile Glu Thr Leu Glu Lys Gly Gly His Thr Ile Arg
            20                  25                  30
Ile Ala His Asp Pro Gln Glu Ile Leu Thr Phe Leu Lys His Asp Ala
        35                  40                  45
Arg Ile Gly Ser Val Leu Cys Thr Leu Asp Ile Phe Asn Arg Glu Leu
    50                  55                  60
Asp Glu Gln Ile Ile Ala Leu Asn Asp Glu Leu Pro Val Phe Ile Leu
65                  70                  75                  80
Lys Pro Thr Asp Cys Asp Lys Pro Val Asp Phe Gly Ala Val Gly Asp
                85                  90                  95
```

```
His Ala Thr Phe Ile Asp Cys His Leu Phe Ser Asn Glu Asp Val Val
            100                 105                 110

Asp Lys Ile Glu Lys Ala Ile Cys His Tyr Ile Asp Asn Ile Thr Pro
        115                 120                 125

Pro Phe Thr Lys Ala Leu Phe Asp Tyr Val Asp Lys Asn Lys Tyr Thr
        130                 135                 140

Phe Cys Thr Pro Gly His Met Ser Gly Thr Ala Phe Leu Lys Ser Pro
145                 150                 155                 160

Val Gly Ser Leu Phe Tyr Asp Phe Tyr Gly Glu Asn Thr Phe Lys Ser
                165                 170                 175

Asp Ile Ser Val Ser Met Gly Glu Leu Gly Ser Leu Leu Asp His Ser
                180                 185                 190

Gly Pro His Lys Glu Ala Glu Tyr Ile Ala Glu Thr Phe Asn Ala
        195                 200                 205

Asp His Ser Tyr Ile Val Thr Asn Gly Thr Ser Thr Ala Asn Lys Ile
        210                 215                 220

Val Gly Met Tyr Ser Val Pro Ala Gly Ser Thr Val Leu Ile Asp Arg
225                 230                 235                 240

Asn Cys His Lys Ser Leu Thr His Leu Leu Met Met Ser Asp Ile Thr
                245                 250                 255

Pro Val Tyr Leu Lys Pro Thr Arg Asn Ala Tyr Gly Ile Leu Gly Gly
                260                 265                 270

Ile Pro Gln Lys Glu Phe Thr Lys Glu Val Ile Thr Glu Lys Leu Thr
        275                 280                 285

Lys Val Pro Gly Ala Thr Trp Pro Val His Ala Val Ile Thr Asn Ser
290                 295                 300

Thr Tyr Asp Gly Leu Phe Tyr Asn Thr Asp Lys Ile Lys Asp Thr Leu
305                 310                 315                 320

Asp Val Lys Ser Ile His Phe Asp Ser Ala Trp Val Pro Tyr Thr Asn
                325                 330                 335

Phe Ser Pro Ile Tyr Asn Gly Lys Thr Gly Met Gly Gly Lys Gln Val
                340                 345                 350

Lys Asp Lys Val Ile Phe Glu Thr His Ser Thr His Ala Leu Leu Ala
        355                 360                 365

Ala Phe Ser Gln Ala Ser Met Ile His Val Lys Gly Asn Leu Asn Thr
        370                 375                 380

Ala Thr Phe Gly Glu Ala Tyr Met Met His Thr Ser Thr Ser Pro Phe
385                 390                 395                 400

Tyr Pro Met Val Ala Ser Thr Glu Val Ala Ala Ala Met Met Arg Gly
                405                 410                 415

Asn Ser Gly Lys Arg Leu Met Gln Asp Ser Leu Glu Arg Ala Val Lys
                420                 425                 430

Phe Arg Lys Glu Ile Lys Lys His Lys Ala His Ala Asp Ser Trp Tyr
        435                 440                 445

Phe Asp Val Trp Gln Pro Glu Asn Val Asp Asn Ile Glu Cys Trp Glu
        450                 455                 460

Leu His Gln Thr Asp Lys Trp His Gly Phe Lys Asp Ile Asp Ala Gln
465                 470                 475                 480

His Met Tyr Leu Asp Pro Ile Lys Val Thr Leu Leu Thr Pro Gly Leu
                485                 490                 495

Asp Lys Asn Gly Glu Leu Glu Lys Thr Gly Ile Pro Ala Asn Leu Val
                500                 505                 510
```

-continued

```
Ser Lys Phe Leu Glu Asp Arg Gly Ile Ile Val Glu Lys Thr Gly Pro
        515                 520                 525

Tyr Asn Ile Leu Val Leu Phe Ser Ile Gly Val Asp Asp Thr Lys Ala
        530                 535                 540

Leu Ser Leu Leu His Ala Leu Asn Glu Phe Lys Ser Leu Tyr Asp Ala
545                 550                 555                 560

Asn Ala Thr Val Glu Glu Val Leu Pro Arg Val Phe Asn Glu Ser Pro
                565                 570                 575

Ser Phe Tyr Gln Glu Met Arg Ile Gln Glu Leu Ala Gln Gly Ile His
            580                 585                 590

Ser Leu Ile Cys Lys His Asn Leu Pro Glu Leu Met Phe Ser Ala Phe
        595                 600                 605

Glu Val Leu Pro Thr Met Val Met Asn Pro His Lys Ala Phe Gln Leu
        610                 615                 620

Glu Leu Lys Gly Gln Ile Glu Asp Cys Tyr Leu Glu Asp Met Val Gly
625                 630                 635                 640

Lys Ile Asn Ala Asn Met Ile Leu Pro Tyr Pro Pro Gly Val Pro Leu
                645                 650                 655

Val Met Pro Gly Glu Met Ile Thr Glu Glu Ser Lys Pro Ile Leu Glu
                660                 665                 670

Phe Leu Met Met Leu Cys Glu Ile Gly Ala His Phe Pro Gly Phe Glu
            675                 680                 685

Thr Asp Ile His Gly Ala Tyr Arg Gln Glu Asp Gly Arg Tyr Lys Val
        690                 695                 700

Lys Ile Val Lys Ala
705
```